(12) United States Patent
Ponce

(10) Patent No.: US 12,727,892 B2
(45) Date of Patent: Sep. 8, 2026

(54) ARTHROSCOPIC DEVICES, SYSTEMS, AND METHODS OF USE

(71) Applicant: Brent Ponce, Lyons, GA (US)

(72) Inventor: Brent Ponce, Lyons, GA (US)

( * ) Notice: Subject to any disclaimer, the term of this patent is extended or adjusted under 35 U.S.C. 154(b) by 179 days.

(21) Appl. No.: 17/500,202

(22) Filed: Oct. 13, 2021

(65) Prior Publication Data

US 2023/0115852 A1 Apr. 13, 2023

(51) Int. Cl.

*A61B 17/17* (2006.01)
*A61B 17/04* (2006.01)
*A61B 17/16* (2006.01)

(52) U.S. Cl.

CPC ...... *A61B 17/1635* (2013.01); *A61B 17/0401* (2013.01); *A61B 17/1778* (2016.11); *A61B 17/1796* (2013.01)

(58) Field of Classification Search

CPC ............... A61B 17/1778; A61F 2/4081; A61F 2002/285

See application file for complete search history.

(56) References Cited

U.S. PATENT DOCUMENTS 4,889,110 A 12/1989 Galline et al.
5,257,996 A 11/1993 McGuire
6,093,190 A 7/2000 Mattchen
6,589,246 B1 7/2003 Hack et al.
7,207,090 B2 4/2007 Mattchen
8,469,967 B2 6/2013 Pratt et al.
8,597,300 B2 * 12/2013 Deffenbaugh ....... A61B 17/683 606/86 R
10,143,506 B2 12/2018 Dreyfuss et al.
10,194,946 B2 * 2/2019 Stecco ................ A61B 17/683
10,405,847 B2 9/2019 Petry et al.
(Continued)

FOREIGN PATENT DOCUMENTS

WO 2005124187 12/2005

OTHER PUBLICATIONS

International Search Report and Written Opinion dated Apr. 17, 2023 of corresponding International Patent Application No. PCT/US2022/046391.

(Continued)

*Primary Examiner* — Eduardo C Robert
*Assistant Examiner* — Steven J Cotroneo
(74) *Attorney, Agent, or Firm* — Bradley Arant Boult Cummings LLP

(57) ABSTRACT

Arthroscopic devices adapted for minimally invasive procedures, such as bone augmentations and reconstructive surgery, are provided. The arthroscopic devices include a drill guide adapted for efficiently and accurately positioning pilot holes and surgical instrumentation relative to the bone; a surgical cable, such as an elastomeric surgical cable, adapted for applying a compressive force across the bone fragments after the surgical repair to promote healing; and a tensioner and crimping device for applying tension to the surgical cable and securing the surgical cable in place. A surgical procedure is also disclosed where a cerclage is applied arthroscopically by passing a member such as an elastomeric ribbon through the glenoid and a bone graft, where the member is tensioned and fixed into place to hold the bone graft in firm contact with the glenoid to facilitate healing.

9 Claims, 22 Drawing Sheets

(56) References Cited

U.S. PATENT DOCUMENTS

| | | | | |
|---|---|---|---|---|
| 10,478,172 | B1* | 11/2019 | Williams | A61B 17/17 |
| 10,561,411 | B1* | 2/2020 | Cole | A61B 17/8869 |
| 10,675,073 | B2* | 6/2020 | Stone | A61B 17/842 |
| 11,432,830 | B2* | 9/2022 | Bosworth | A61B 17/842 |
| 2003/0236555 | A1* | 12/2003 | Thornes | A61B 17/842 606/232 |
| 2004/0254585 | A1* | 12/2004 | Whittaker | A61B 17/1714 606/104 |
| 2012/0310279 | A1* | 12/2012 | Sikora | A61B 17/0401 606/232 |
| 2013/0023942 | A1* | 1/2013 | Wyman | A61B 17/1697 606/86 R |
| 2013/0066371 | A1* | 3/2013 | Rogers | A61F 2/4081 606/232 |
| 2013/0325011 | A1* | 12/2013 | Cleveland | A61B 17/16 606/86 R |
| 2019/0201206 | A1* | 7/2019 | Bettenga | A61F 2/30734 |
| 2019/0282283 | A1 | 9/2019 | Dooney et al. | |
| 2019/0307568 | A1* | 10/2019 | Bettenga | A61B 17/683 |
| 2019/0350578 | A1 | 11/2019 | Petry et al. | |
| 2021/0015504 | A1* | 1/2021 | Castricini | A61B 17/1796 |
| 2021/0113343 | A1 | 4/2021 | Ponce et al. | |
| 2023/0301699 | A1* | 9/2023 | Cole | A61B 17/8869 606/74 |

OTHER PUBLICATIONS

Meraner, D et al., “10 Years of Arthroscopic Latarjet Procedure: Outcome and Complications,” 2019 Indian J Orthop, vol. 53, Issue 1, pp. 102-110.

Rollick, N et al., “Long-term outcomes of the Bankart and Latarjet repairs: a systematic review,” 2017 Open Access J Sports Med, vol. 8, pp. 97-105.

Bonazza, N et al., “Trends in Surgical Management of Shoulder Instability,” 2017 Ortho J Sports Med, pp. 1-7.

* cited by examiner

ARTHROSCOPIC DEVICES, SYSTEMS, AND METHODS OF USE

TECHNICAL FIELD

The present disclosure relates generally to surgical devices, systems, and methods for use in performing minimally invasive procedures, such as arthroscopic procedures.

BACKGROUND

Shoulder instability is a common orthopedic condition where the humeral head separates from the glenoid (socket). This can be a very quick partial separation that lasts only momentarily (subluxation), or it can be a more significant condition where the humeral head and the glenoid become stuck in the dislocated position. When shoulder instability events occur, they can cause damage to the shoulder including tears of the labrum (rim of soft cartilage tissue around the socket), cartilage injuries, rotator cuff tears, or even fractures. Glenoid or socket bone loss, which results from impaction of the humeral head against the anterior glenoid rim, is also common following shoulder dislocation. Shoulder instability frequently requires surgery for patients who suffer pain and physical limitations.

The most common surgical techniques for the treatment of recurrent anterior shoulder instability include the arthroscopic soft tissue (Bankart) repair, the open soft tissue repair, and the open bone transfer procedure. However, these conventional shoulder stabilization surgical techniques have limitations. There is a particularly high rate of complications with these surgical techniques, including superficial infection, superficial vein thrombosis, musculocutaneous neuropraxia, graft non-union, graft resorption, graft mal-union graft migration, and intra-articular hardware. Additionally, patients having surgery for anterior shoulder instability may experience post-operative dislocation, suffer from recurrent instability, and develop glenohumeral arthritis.

More recently, arthroscopic glenoid bone augmentation fixation has been described for repairing glenoid bone loss. This new surgical technique, however, also has challenges. In particular, this surgical technique requires the use of screws or sutures for the glenoid implant fixation. While the use of screws provides for sufficient fixation, the hardware is difficult to insert during surgery. With the use of sutures or buttons, there is a risk of fracture due to the lack of dispersion of forces across the implant. Moreover, when sutures or buttons are used, there is a lack of appropriate control of the implant without the use of some type of spike or peg. Due to these limitations, arthroscopic glenoid bone augment techniques are not widely used.

Accordingly, there remains a need in the art for an improved arthroscopic glenoid bone augmentation surgical technique with improved surgical devices that provide for less complex surgeries to limit surgical morbidity and complications and that better restore the natural anatomy and biomechanics of the joint.

SUMMARY

The problems expounded above, as well as others, are addressed by the following inventions, although it is to be understood that not every embodiment of the inventions described herein will address each of the problems described above.

In a first aspect, a drill guide is provided, the drill guide including a body having a proximal end and a distal end, the distal end configured for engaging a bone, wherein the body includes a first drill guide opening extending therethrough and an outer surface having a first slot formed therein; a tab configured for slidable insertion into the first slot to a position in which the tab is aligned with a rim of the bone and in parallel alignment with the drill guide opening; and wherein the drill guide opening is offset from the first slot by about 1 mm to about 8 mm.

In a second aspect, a drill guide is provided, the drill guide including a body having a proximal end and a distal end, the distal end configured for engaging a bone, wherein the body includes an outer surface having a first slot and a second slot formed therein; a first tab configured for slidable insertion into the first slot to a position in which the tab is engaged with the bone, wherein the first tab includes a drill guide opening extending therethrough; and a second tab configured for slidable insertion into the second slot to a position in which the second tab is aligned with a rim of the bone and in parallel alignment with the first tab.

In a third aspect, a surgical elastomeric cable is provided, the surgical elastomeric cable including a body portion having a generally flat, planar outer surface and formed of an elastic polymer material, the elastic polymer material configured to be tensioned to a working length that is longer than a pre-tensioned length.

In a fourth aspect, a tensioner and crimping device is provided, the tensioner and crimping device including a housing having a proximal end and a distal end; a nose attached to the distal end of the housing, wherein the nose includes a shaft positioned therein, the shaft including a releasable securing member configured for engagement with a crimping member seated within the nose; a tensioning mechanism operatively attached to the housing and configured to apply tension to a surgical cable extending through the crimping member and the shaft; and a lever actuator operatively attached to the shaft and configured to move the shaft in a direction toward the crimping member and release the securing member upon engagement with the crimping member.

In a fifth aspect, a tensioner and crimping device is provided, the tensioner and crimping device including a housing having a proximal end and a distal end; a nose attached to the distal end of the housing, wherein the nose includes a shaft positioned therein, the shaft including a releasable securing member attached thereto and having a plurality of barbs extending radially therefrom; a crimping member seated within the nose and including a female receptacle having a plurality of grooves configured for engagement with the plurality of barbs on the releasable securing member; a pair of wires releasably attached to the crimping member and extending through the nose along opposing sides of the shaft; a tensioning mechanism operatively attached to the housing and configured to apply tension to a surgical cable extending through the housing, the shaft, and the crimping member; and a lever actuator operatively attached to the shaft and configured to move the shaft in a direction toward the crimping member and release the securing member upon engagement with the female receptacle of the crimping member.

In a sixth aspect, a method of performing an arthroscopic bone augmentation surgery is provided, the method including drilling a pilot hole into a bone in need of augmentation surgery, wherein the drilling is performed from a first side to a second side; passing a surgical cable through the pilot hole from the first side to the second side and into a graft; tensioning the surgical cable to a setting sufficient to apply a compressive force to the bone and the graft; and securing a crimping member one each end of the surgical cable to preserve the applied compressive force.

In a seventh aspect, a method of performing an arthroscopic bone augmentation surgery is provided, the method including drilling a pilot hole into a bone in need of augmentation surgery, wherein the drilling is performed from a first side to a second side; passing a fixation device with surgical cable looped therethrough through the pilot hole from the first side to the second side and positioning the fixation device onto a surface of the bone on the second side; tensioning the surgical cable to a setting sufficient to apply a compressive force to the fixation device; and securing a crimping member to the surgical cable on the first side to preserve the applied compressive force.

In an eighth aspect, a method of performing an arthroscopic bone augmentation surgery is provided, the method including drilling a first pilot hole and a second pilot hole into a bone in need of augmentation surgery, wherein the drilling is performed from a first side to a second side; passing a surgical cable through the first pilot hole from the first side to the second side; looping the surgical cable through a graft operatively attached to a suture glide plate; passing the surgical cable through the second pilot hole from the second side to the first side; tensioning the surgical cable to a setting sufficient to apply a compressive force to the bone and the graft; and securing a crimping member to the surgical cable to preserve the applied compressive force.

In a ninth aspect, a system for performing arthroscopic surgery is provided, the system including a surgical cable; a drill guide including a body having a proximal end and a distal end, the distal end configured for engaging a bone, wherein the body includes a first drill guide opening extending therethrough and an outer surface having a first slot formed therein; a tab configured for slidable insertion into the first slot to a position in which the tab is aligned with a rim of the bone and in parallel alignment with the drill guide opening; wherein the drill guide opening is offset from the first slot by about 1 mm to about 8 mm; and a tensioner and crimping device including a housing having a proximal end and a distal end; a nose attached to the distal end of the housing, wherein the nose includes a shaft positioned therein, the shaft including a releasable securing member configured for engagement with a crimping member seated within the nose; a tensioning mechanism operatively attached to the housing and configured to apply tension to the surgical elastomeric cable extending through the crimping member and the shaft; and a lever actuator operatively attached to the shaft and configured to move the shaft in a direction toward the crimping member and release the securing member upon engagement with the crimping member.

In a tenth aspect, a system for performing arthroscopic surgery is provided, the system including a surgical cable; a drill guide including a body having a proximal end and a distal end, the distal end configured for engaging a bone, wherein the body includes an outer surface having a first slot and a second slot formed therein; a first tab configured for slidable insertion into the first slot to a position in which the tab is engaged with the bone, wherein the first tab includes a drill guide opening extending therethrough; and a second tab configured for slidable insertion into the second slot to a position in which the second tab is aligned with a rim of the bone and in parallel alignment with the first tab; and a tensioner and crimping device including a housing having a proximal end and a distal end; a nose attached to the distal end of the housing, wherein the nose includes a shaft positioned therein, the shaft including a releasable securing member configured for engagement with a crimping member seated within the nose; a tensioning mechanism operatively attached to the housing and configured to apply tension to the surgical elastomeric cable extending through the crimping member and the shaft; and a lever actuator operatively attached to the shaft and configured to move the shaft in a direction toward the crimping member and release the securing member upon engagement with the crimping member.

BRIEF DESCRIPTION OF THE DRAWINGS

Further features and advantages can be ascertained from the following detailed description that is provided in connection with the drawings described below.

DETAILED DESCRIPTION

Figure 1A:
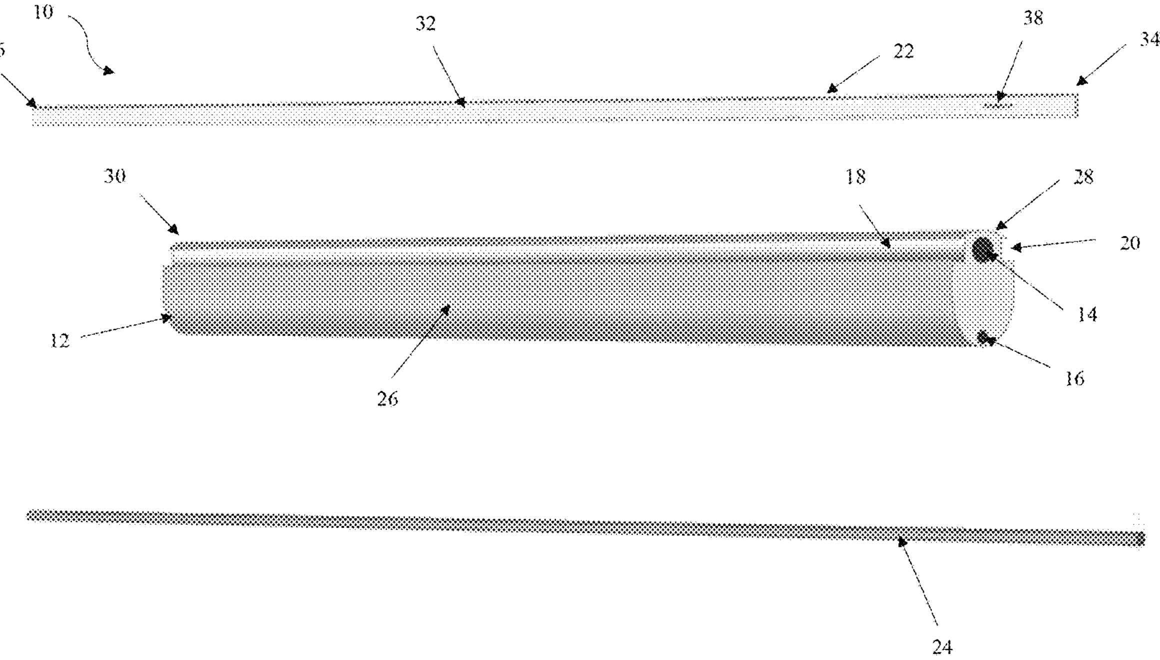
FIG. 1A is an exploded view of a drill guide according to an exemplary embodiment of the present disclosure.

Unless otherwise defined, all terms (including technical and scientific terms) used herein have the same meaning as commonly understood by one of ordinary skill in the art of this disclosure. It will be further understood that terms, such as those defined in commonly used dictionaries, should be interpreted as having a meaning that is consistent with their meaning in the context of the specification and should not be interpreted in an idealized or overly formal sense unless expressly so defined herein. Well known functions or constructions may not be described in detail for brevity or clarity.

The terms "about" and "approximately" shall generally mean an acceptable degree of error or variation for the quantity measured given the nature or precision of the measurements. Typical, exemplary degrees of error or variation are within 20 percent (%), preferably within 10%, more preferably within 5%, and still more preferably within 1% of a given value or range of values. Numerical quantities given in this description are approximate unless stated otherwise, meaning that the term "about" or "approximately" can be inferred when not expressly stated.

The terminology used herein is for the purpose of describing particular embodiments only and is not intended to be limiting. As used herein, the singular forms "a", "an" and "the" are intended to include the plural (i.e., "at least one") forms as well, unless the context clearly indicates otherwise.

The terms "first," "second," "third," and the like are used herein to describe various features or elements, but these features or elements should not be limited by these terms. These terms are only used to distinguish one feature or element from another feature or element. Thus, a first feature or element discussed below could be termed a second feature or element, and similarly, a second feature or element discussed below could be termed a first feature or element without departing from the teachings of the present disclosure.

Spatially relative terms, such as "above," "under," "below," "lower," "over," "upper," and the like, may be used herein for ease of description to describe one element or feature's relationship to another when the apparatus is right side up as shown in the accompanying drawings.

Terms such as "at least one of A and B" should be understood to mean "only A, only B, or both A and B." The same construction should be applied to longer lists (e.g., "at least one of A, B, and C").

The term "may" as used herein refers to features that are optional (i.e., "may or may not,"), and should not be construed to limit what is described.

In the drawings and in the description which follows, the term "proximal" will refer to the end of the surgical device which is closest to the operator, while the term "distal" will refer to the end of the device which is furthest from the operator.

It is to be understood that any given elements of the disclosed embodiments of the invention may be embodied in a single structure, a single step, a single substance, or the like. Similarly, a given element of the disclosed embodiment may be embodied in multiple structures, steps, substances, or the like.

The present disclosure provides surgical devices, systems, and methods for use in performing arthroscopic procedures or other similar procedures, for example, bone augmentations and reconstructive surgery for repairing musculoskeletal tissue. In some embodiments, the surgical devices, systems, and methods are particularly suitable for arthroscopic glenoid augmentation surgery. However, the systems and methods of the present disclosure are not limited to arthroscopy and can further be used in endoscopic and laparoscopic procedures as well as open surgeries and robotic surgical procedures.

DEVICES AND SYSTEMS

The present disclosure provides for arthroscopic devices adapted for minimally invasive procedures, such as bone augmentations and reconstructive surgery, for example, arthroscopic glenoid augmentation surgery. As will be described in detail below, the arthroscopic devices of the present disclosure include a drill guide adapted for efficiently and accurately positioning pilot holes and surgical instrumentation relative to the bone; a surgical cable, such as an elastomeric surgical cable, adapted for applying a compressive force across the bone fragments after the surgical repair to promote healing; and a tensioner and crimping device having a crimping member positioned therein for applying tension to the surgical cable once it has been wrapped around the bone fragments and securing the surgical cable in place with the described crimping member. In some embodiments, the arthroscopic devices described herein can be adapted as a system for performing arthroscopic bone augmentations and reconstructive surgery. For example, the drill guide, the surgical cable, the crimping member, and the tensioner and crimping device of the present disclosure may be used with conventional surgical instrumentation, such as bone harvesting instrumentation, shuttling sutures, cable cutters, and tissue spreading devices, to perform an arthroscopic glenoid augmentation surgery. A surgical procedure is disclosed, wherein a cerclage is applied arthroscopically, utilizing a posterior and an anterior cannula, by passing a member such as an elastomeric ribbon through the first of two parallel holes in the glenoid aligned with complementary holes in a bone graft and back through the second of the parallel holes in the bone graft and glenoid, wherein the member is tensioned and fixed into place to hold the bone graft in firm contact with the glenoid to facilitate healing. The techniques described herein may also be applied in setting of open bone transfer procedures. These procedures may utilize the drill guides, cable, and tensioner and crimping device disclosed herein, but do not require cannula utilization or components of arthroscopic suture and bone passage.

Drill Guide

Figure 1B:
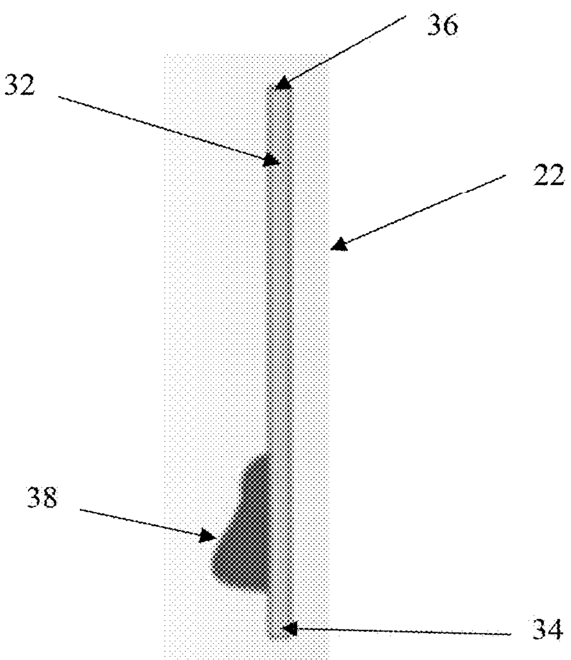
FIG. 1B is a side view of a tab for use with the drill guide according to an embodiment of the present disclosure.
Figure 1C:
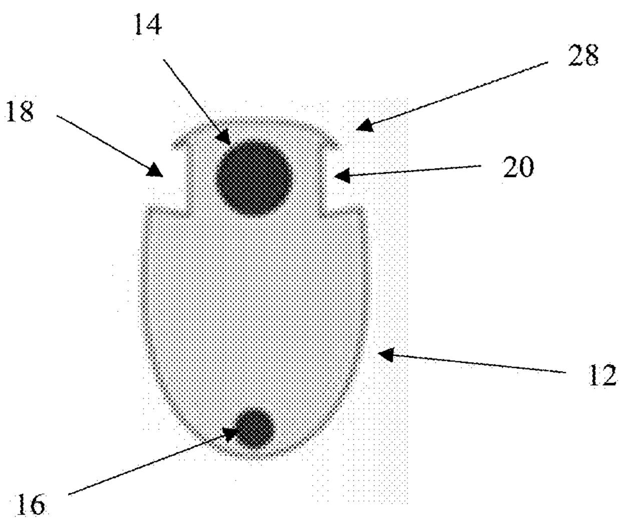
FIG. 1C is a front view of the drill guide according to an embodiment of the present disclosure.

The present disclosure provides an offset drill guide adapted for arthroscopic procedures and particularly adapted for the drilling of parallel holes. Referring to FIGS. 1A-1C, a drill guide 10 having a single barrel according to one embodiment of the present disclosure is shown. As shown in FIG. 1A, the drill guide 10 includes a tubular elongated body 12 having a proximal end 28 and a distal end 30. The elongated body 12 is adapted to fit within a cannula during arthroscopic surgery such that the distal end 30 engages the face of the bone (for example, the glenoid). The elongated body 12 includes a single drill guide opening 14 that extends through the elongated body 12 so as to form a substantially tubular hole for receiving a drill bit (not shown). The elongated body 12 also includes a wire guide opening 16 that extends through the elongated body 12 so as to form a substantially tubular hole for receiving a guide wire 24, such as K-wire, to help hold the drill guide 10 in place during use. The elongated body 12 further includes a first slot 18 and a second slot 20 formed along an outer surface 26 of the elongated body 12. Each of the first and second slots 18, 20 extends along a longitudinal axis of the elongated body 12 from the proximal end 28 to the distal end 30. In the illustrated embodiment, the first slot 18 is in parallel alignment with the second slot 20. The elongated body 12 may have any length sufficient to allow for the drill guide 10 to extend through the cannula and engage the bone. In one embodiment, the elongated body 12 is at least about 10 cm in length. In another embodiment, the elongated body 12 is at least about 12 cm in length. For example, the elongated body 12 may be about 13 cm in length.

As illustrated in FIGS. 1A and 1, the drill guide 10 also includes a tab 22. The tab 22 is configured to be slidably positioned within the first slot 18 or the second slot 20. When the tab 22 is inserted into the first slot 18 or the second slot 20, the tab 22 slides along the first slot 18 or the second slot 20 to a position in which the tab 22 is held flush along the face of the bone (for example, the glenoid) and in parallel alignment with the drill guide opening 14. This positioning of the tab 22 allows for proper alignment selection of the pilot holes by the surgeon. The tab 22 also allows for the pilot holes to be offset from the flat face of the glenoid. In the illustrated embodiment, the tab 22 has a rectangular cross section that is complementary in shape to the outline of the first and second slots 18, 20 for ease of insertion. In some embodiments, the tab 22 may have an outer surface 32 that tapers inwardly from a proximal end 34 to a distal end 36. The tapered design acts as a stopping mechanism to prevent the proximal end 34 of the tab 22 from sliding entirely through the slot 18, 20. The tab 22 may have any thickness sufficient to allow for slidable movement within the first slot 18 and the second slot 20. In one embodiment, the tab 22 may have a thickness of about 2 mm to about 4 mm. In another embodiment, the tab 22 may have a thickness of about 3 mm. As shown in FIG. 1B, the tab 22 may further include a notch 38. The notch 38 may be positioned on the proximal end 34 of the tab 22.

FIG. 1C shows the proximal end 28 of the elongated body 12. As shown in FIG. 1C, the proximal end 28 has a substantially flat, planar surface with the drill guide opening 14 positioned above the wire guide opening 16. In one embodiment, the distance between the drill guide opening 14 and the wire guide opening 16 is about 12 mm or less. In another embodiment, the distance between the drill guide opening 14 and the wire guide opening 16 is about 10 mm or less. In still another embodiment, the distance between the drill guide opening 14 and the wire guide opening 16 is about 8 mm or less.

Additionally, as shown in FIG. 1C, the drill guide opening 14 is offset from the first slot 18 and the second slot 20 by a predetermined distance. In one embodiment, the drill guide opening 14 may be offset from each of the first slot 18 and the second slot 20 by a predetermined distance of about 1 mm to about 4 mm. In another embodiment, the drill guide opening 14 may be offset from each of the first slot 18 and the second slot 20 by a predetermined distance of about 2 mm to about 3 mm. For example, the drill guide opening 14 may be offset from each of the first slot 18 and the second slot 20 by a predetermined distance of about 2.5 mm. The width of each of the drill guide opening 14 and the wire guide opening 16 may also vary depending on the size of the drill, suture guide, and wire to be used during surgery. In one embodiment, the drill guide opening 14 may have a width of at least 2 mm, preferably at least 3 mm. In another embodiment, the drill guide opening 14 may have a width of about 3 mm to about 8 mm.

Figure 1D:
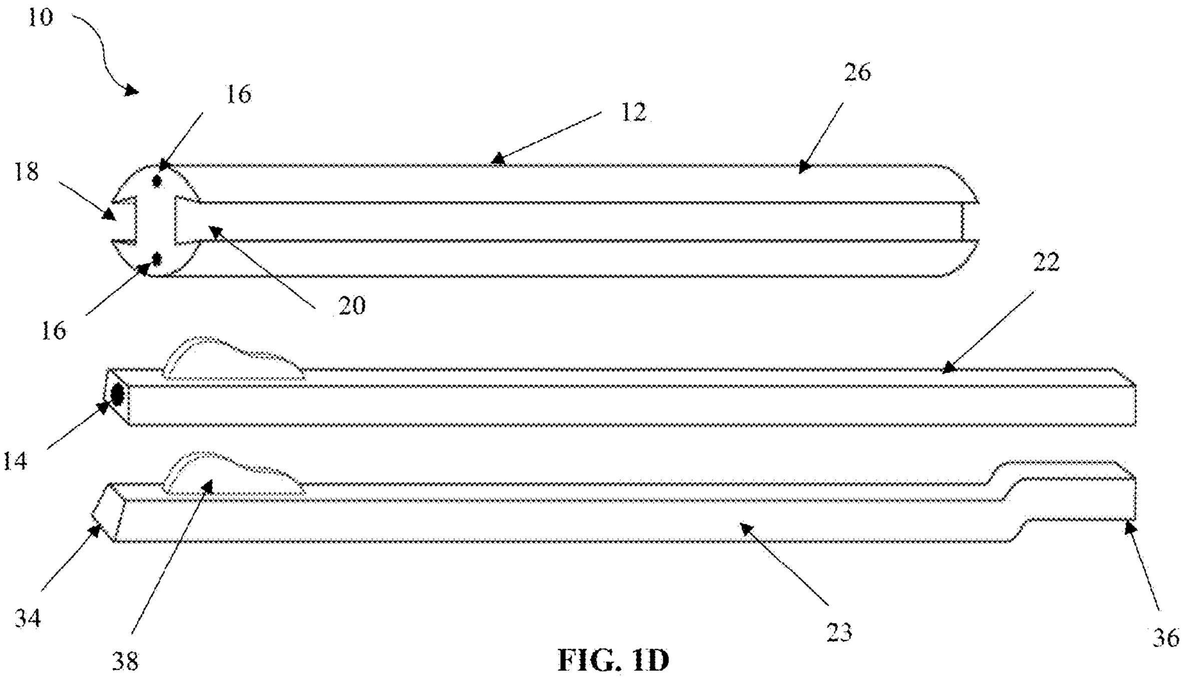
FIG. 1D is an exploded view of a drill guide according to another embodiment of the present disclosure.
Figure 1E:
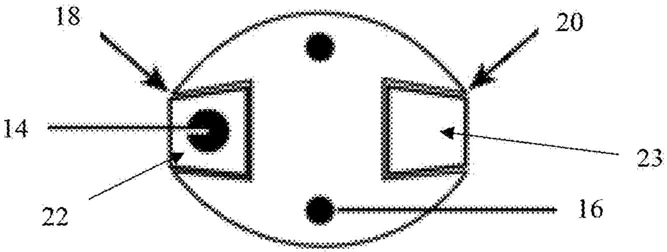
FIG. 1E is a front view of the drill guide shown in FIG. 1D according to an embodiment of the present disclosure.

FIGS. 1D and 1E show the drill guide 10 according to another single barrel embodiment of the present disclosure. In the illustrated embodiment, the drill guide 10 includes the elongated body 12 having the first slot 18 and the second slot 20 formed along the outer surface 26. The elongated body 12 also includes two wire guide openings 16 for receiving the guide wire 24. However, in this embodiment, the drill guide opening 14 is positioned in the tab 22 rather than in the elongated body 12. As shown in FIGS. 1D and 1E, the drill guide 10 includes the tab 22 having the drill guide opening 14 extending therethrough and a second tab 23. Each of the tab 22 and the second tab 23 includes the notch 38 positioned on the proximal end 34.

In practice, as will be described in more detail below, the tab 22 with the drill guide opening 14 extending therethrough is inserted into the first slot 18 to a position in which the tab 22 directly contacts the face of the bone, while the second tab 23 is inserted into the second slot 20 to a position in which the second tab 23 is held flush along the face of the bone and in parallel alignment with the tab 22. In some embodiments, as shown in FIG. 1D, the distal end 36 of the second tab 23 may protrude outwardly to create a notch that allows for the second tab 23 to securely align with the outer rim of the bone while a drill bit is received in the drill guide opening 14.

Figure 1F:
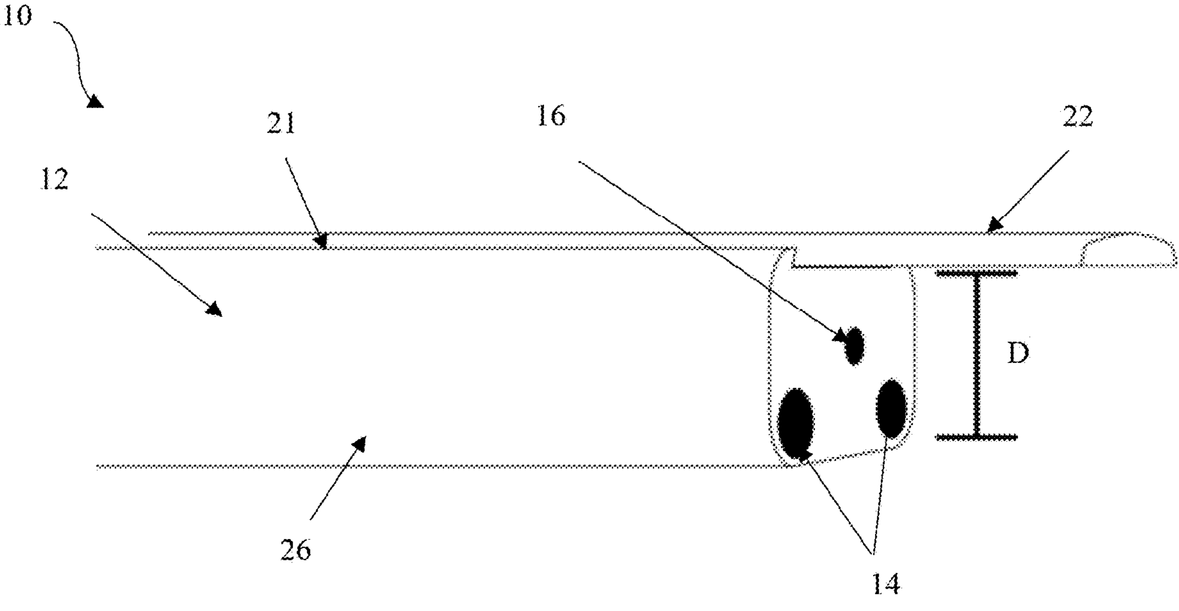
FIG. 1F is a side view of a drill guide according to still another embodiment of the present disclosure.
Figure 1G:
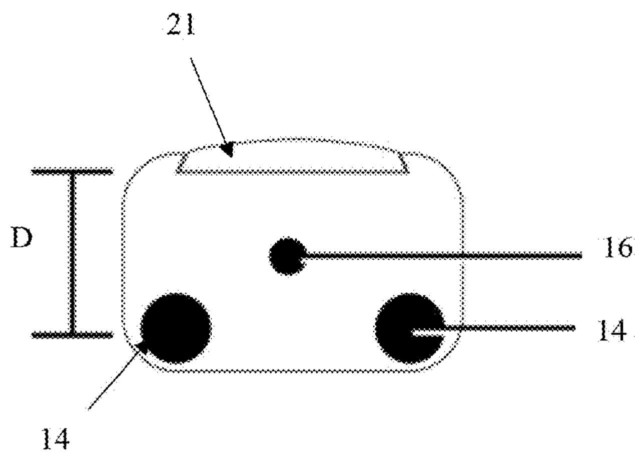
FIG. 1G is a front view of the drill guide shown in FIG. 1F according to an embodiment of the present disclosure.

FIGS. 1F and 1G show the drill guide 10 according to still another embodiment of the present disclosure. The drill guide 10 shown in FIGS. 1F and 1G is a double barrel drill guide. In the illustrated embodiment, the drill guide 10 includes the elongated body 12 having two drill guide openings 14 extending therethrough. The use of a double barrel drill guide is advantageous in that it allows two pilot holes to be formed without having to perform the additional step of rotating the drill guide. In this embodiment, the drill guide openings 14 are positioned in a substantially parallel configuration. The wire guide opening 16 for receiving the guide wire 24 may be positioned in the center of the elongated body 12. As shown in FIGS. 1F and 1G, the elongated body 12 has a single slot 21 formed along the outer surface 26 of the elongated body 12. The slot 21 is configured for receiving the tab 22 therein, as described above.

In the double barrel embodiment, the drill guide openings 14 are offset from the slot 21 by a predetermined distance "D". In one embodiment, the drill guide openings 14 may be offset from the slot 21 by a predetermined distance "D" of about 1 cm to about 10 cm. In another embodiment, the drill guide openings 14 may be offset from the slot 21 by a predetermined distance "D" of about 3 cm to about 8 cm. In still another embodiment, the drill guide openings 14 may be offset from the slot 21 by a predetermined distance "D" of about 4 cm to about 7 cm. For example, the drill guide openings 14 may be offset from the slot 21 by a predetermined distance "D" of about 6 cm.

Figure 2A:
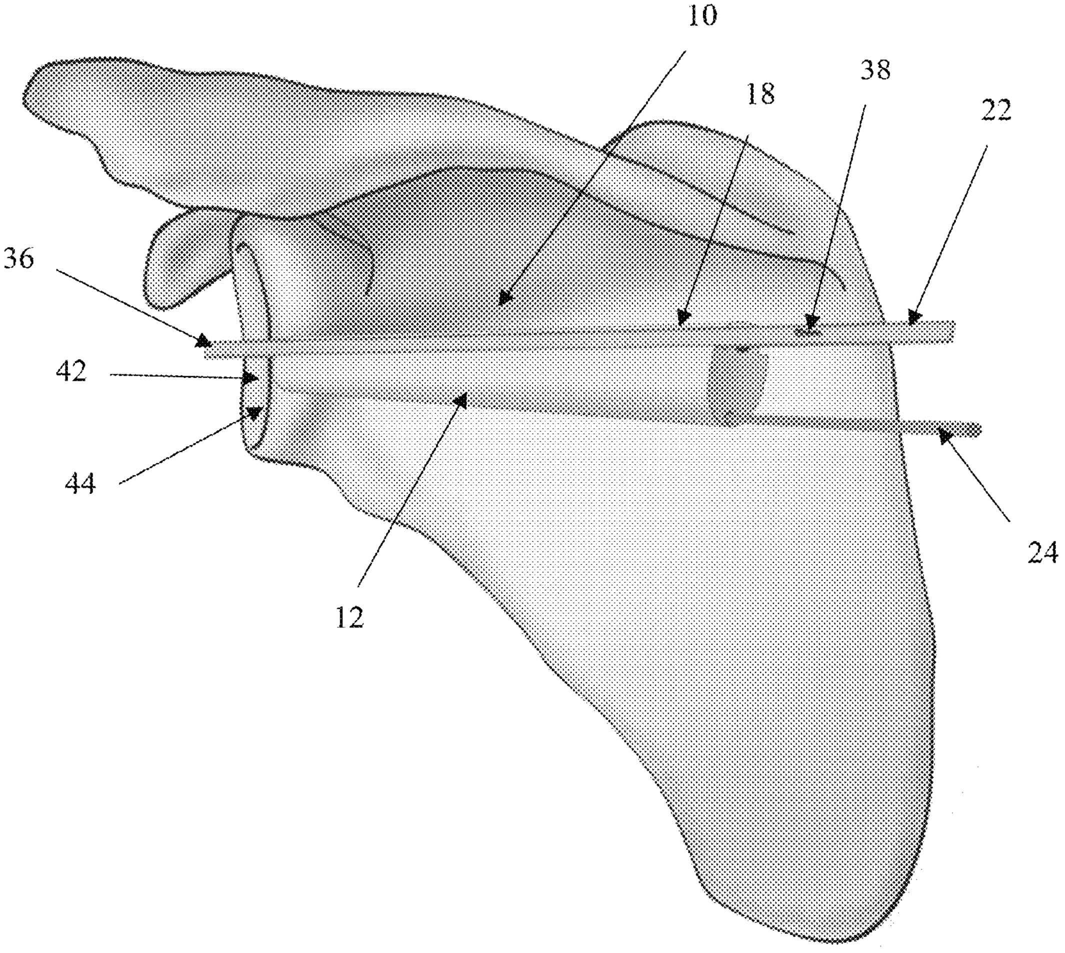
FIG. 2A is a schematic showing the drill guide according to an embodiment of the present disclosure aligned with the rim of a glenoid.

FIG. 2A shows the assembled drill guide 10 aligned with a rim 44 of a glenoid 42 and ready for use, according to one embodiment of the present disclosure. In practice, a posterior portal is opened for a generally forward-directed cannula (not shown). The forwarded-directed cannula provides access to the surgical site by the drill guide 10 of the present disclosure. The drill guide 10 is inserted through the posterior cannula into the proximity of the surgical site. As shown in FIG. 2, the tab 22 is inserted through the first slot 18 to a length sufficient to allow the distal end 36 of the tab 22 to align with the rim 44 of the glenoid 42, while the elongated body 12 is aligned with the glenoid 42. Alignment of the distal end 36 of the tab 22 along the rim 44 allows for precise placement of the elongated body 12 and the corresponding pilot holes. In some embodiments, the guide wire 24 may be inserted through the wire guide opening 16 and engaged with the glenoid 42 to provide additional stability of the drill guide 10. Once the tab 22, and preferably, the guide wire 24, have been positioned within the drill guide 10, a drill bit (not shown) may be inserted through the drill guide opening 14 to create a first pilot hole in the glenoid 42. To create a second pilot hole in the glenoid 42, the tab 22 may be removed from the first slot 18 and the elongated body 12 may be rotated about an axis defined by the guide wire 24 to a desired degree of rotation. In some embodiments, the elongated body 12 is rotated 180 degrees about the axis defined by the guide wire 24 to create a second pilot hole that is substantially parallel to the first pilot hole. Once the elongated body 12 is rotated and positioned for placement of the second pilot hole, the tab 22 is inserted through the second slot 20 to a length sufficient to allow the distal end 36 of the tab 22 to align with the rim 44 of the glenoid 42. Once the tab 22 has been positioned within the drill guide 10, a drill bit (not shown) may be inserted through the drill guide opening 14 to create a second pilot hole in the glenoid 42.

Figure 2B:
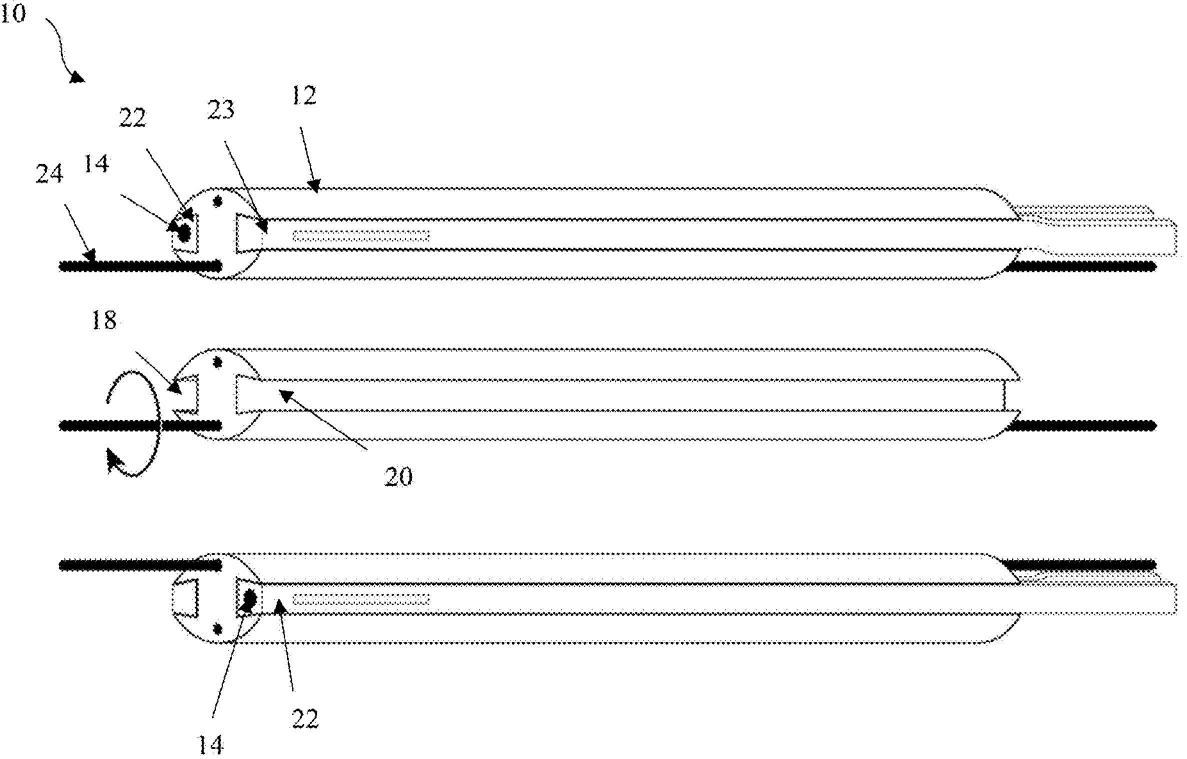
FIG. 2B is a schematic drawing showing the use of the drill guide according to another embodiment of the present disclosure.

FIG. 2B shows the assembled drill guide 10 ready for use according to another embodiment of the present disclosure. The assembled drill guide 10 shown in FIG. 2B is a single barrel drill guide having the drill guide opening 14 extending through the tab 22. In use, the tab 22 with the drill guide opening 14 extending therethrough is inserted through the first slot 18 to a position in which the tab 22 directly contacts the face of the bone, such as the glenoid 42. The second tab 23 is then inserted into the second slot 20 to a position in which the second tab 23 is aligned with the rim 44 of the glenoid 42. In some embodiments, guide wires 24 may be inserted through the wire guide openings 16 and engaged with the glenoid 42 to provide additional stability of the drill guide 10. Once the tabs 22, 23, and preferably, the guide wire 24, have been positioned within the drill guide 10, a drill bit (not shown) may be inserted through the drill guide opening 14 in the tab 22 to create a first pilot hole in the glenoid 42. To create a second pilot hole in the glenoid 42, the tabs 22, 23 are removed from the first slot 18 and the second slot 20 and the elongated body 12 may be rotated about the axis defined by the guide wire 24. Once the elongated body 12 is rotated and positioned for placement of the second pilot hole, the tab 22 is inserted into the rotated first slot 18 to create a second pilot hole in the glenoid 42.

Figure 3:
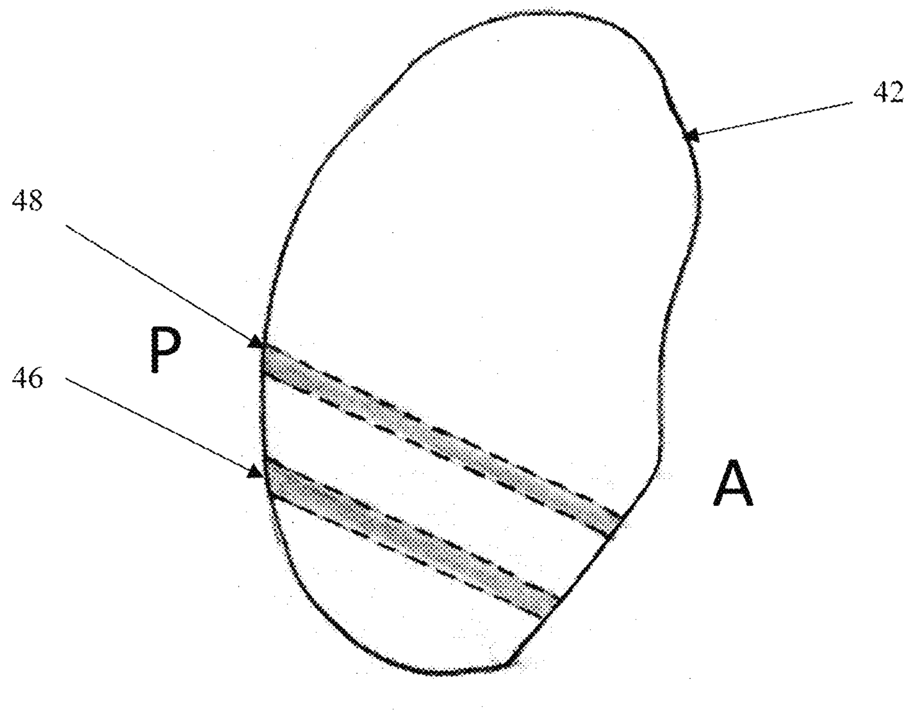
FIG. 3 is a schematic showing two pilot holes formed in the glenoid using the drill guide of the present disclosure.

FIG. 3 shows the glenoid 42 having a first pilot hole 46 and a second pilot hole 48 drilled therein by the drill guide 10 of the present disclosure. As shown in FIG. 3, each of the first pilot hole 46 and the second pilot hole 48 are drilled through the glenoid 42 and extend from the posterior side P to the anterior side A. The drill guide 10 advantageously results in the precise placement and alignment of parallel pilot holes. As described above, the distance between each pilot hole 46, 48 will vary depending upon the predetermined offset distance (i.e., the distance between the drill guide opening 14 and the longitudinal guide center line 40) and the width of the anterior graft.

Ribbon Cable

The present disclosure also provides a novel ribbon cable for securing the anterior graft to the glenoid 42 and applying a compressive force across the glenoid 42 and the anterior graft after the surgical repair to promote healing. In one embodiment, the ribbon cable has elastomeric properties that allow for the ribbon cable to apply a constant compressive force across the glenoid and the anterior graft after the surgical repair. In other embodiments, the ribbon cable may be static such that the ribbon cable has substantially no elasticity. For example, the ribbon cable may be any metallic surgical grade cable, such as a stainless-steel surgical cable.

Figure 4:
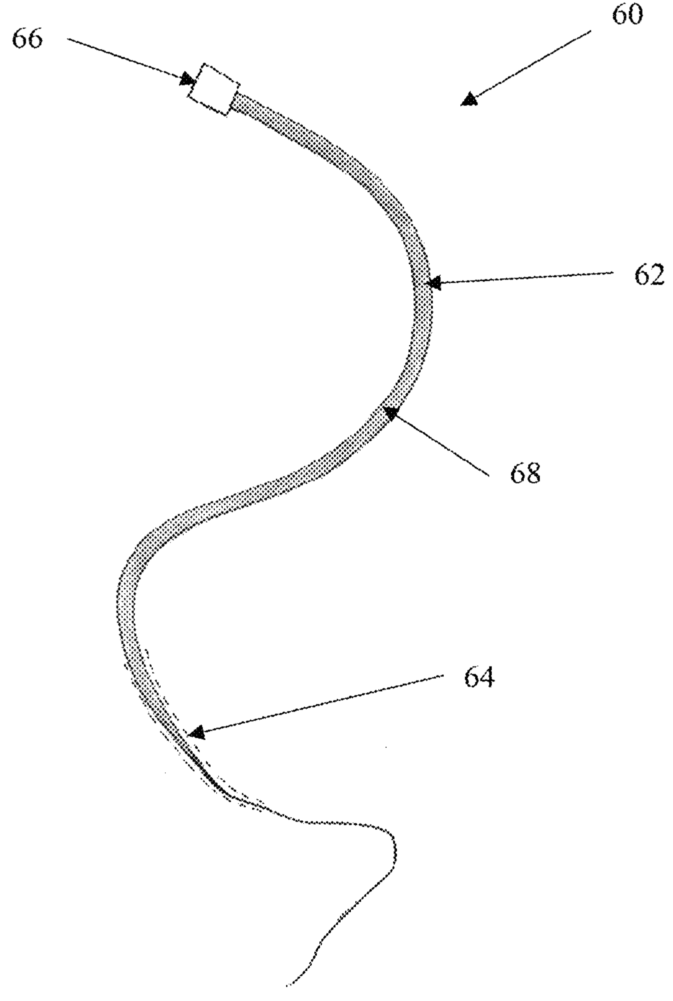
FIG. 4 is a perspective view of a surgical ribbon cable according to an embodiment of the present disclosure.

FIG. 4 shows an exemplary embodiment of an elastomeric ribbon 60 contemplated by the present disclosure. As shown in FIG. 4, the elastomeric ribbon 60 includes a body portion 62 and a tail end portion 64. The body portion 60 has a generally flat, planar outer surface 68. The outer surface 68 may vary in width and thickness depending on the surgical application. In one embodiment, the outer surface 68 may have a width ranging from about 0.5 mm to about 3 mm. In another embodiment, the outer surface 68 may have a width ranging from about 1 mm to about 2 mm. In still another embodiment, the outer surface 68 may have a width of about 1.5 mm. The tail end portion 64 is tapered in its width to allow for the elastomeric ribbon 60 to easily pass through the pilot holes 46, 48. For instance, the tail end portion 64 may have a width that is 15 percent of the width of the body portion 60. In another embodiment, the tail end portion 64 may have a width that is 10 percent of the width of the body portion 60. In still another embodiment, the tail end portion 64 may have a width that is 5 percent of the width of the body portion 60. In one embodiment, the tail end portion 64 is formed of the same elastic polymer material as the body portion 62 but is tapered in its width. In another embodiment, the tail end portion 64 is a suture that is attached to the body portion 62. For example, the tail end portion 64 may be a #5 suture designed for orthopedic use. In other embodiments, the suture may be an ultra-high-molecular weight polyethylene suture having a varying width. As shown in FIG. 4, the end of the body portion 62 opposite the tail end portion 64 may be operatively attached to a crimping member 66, as will be described in more detail below.

The elastomeric ribbon 60 may be formed of any type of elastic polymer material that has sufficient strength to hold bone fragments together and maintain proper positioning of the fragments during healing yet elastic enough to allow for natural movement of the bones. In one embodiment, the elastomeric ribbon 60 may be formed of a polymeric material, such as nylon, polyester, polyethylene, or fluorocarbon. The elastomeric ribbon 60 may also include an outer coating. For instance, the outer coating may be polyethylene, polyester, silicone or any material suitable to protect and/or enhance the performance of elastomeric ribbon 60.

The elastomeric ribbon 60 has certain elastic properties that allow for the elastomeric ribbon to be stretched or tensioned to a working length which is longer than its pre-tensioned original length. In one embodiment, the elastomeric ribbon 60 may have an elongation ranging from about 30 percent to about 150 percent of its original length. In another embodiment, the elastomeric ribbon 60 may have an elongation ranging from about 50 percent to about 100 percent of its original length. In other embodiments, the elastomeric ribbon 60 may have an axial stiffness of about 5 to 20 Newtons (N) per millimeter. For instance, the elastomeric ribbon 60 may have an axial stiffness of about 10 to 15 N per millimeter. The elastomeric ribbon 60 can be set at medically accepted loads, for instance, of about 400 to 800 N, to provide a continuous active compressive force across the mating bone fragments. For instance, the elastomeric ribbon 60 can be set at a medically accepted load of about 550 N to provide a continuous active compressive force across the mating bone fragments.

Figure 5:
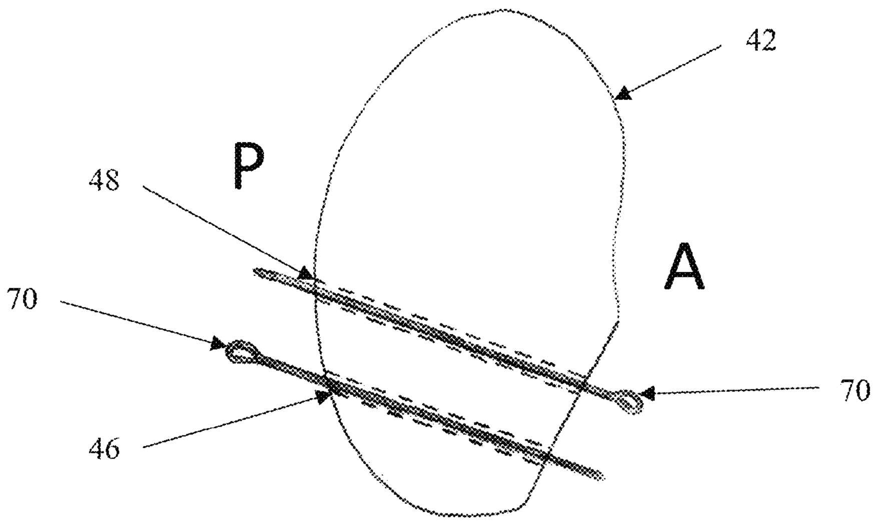
FIG. 5 is a schematic showing a shuttling suture passed through each of the pilot holes formed in the glenoid.
Figure 6:
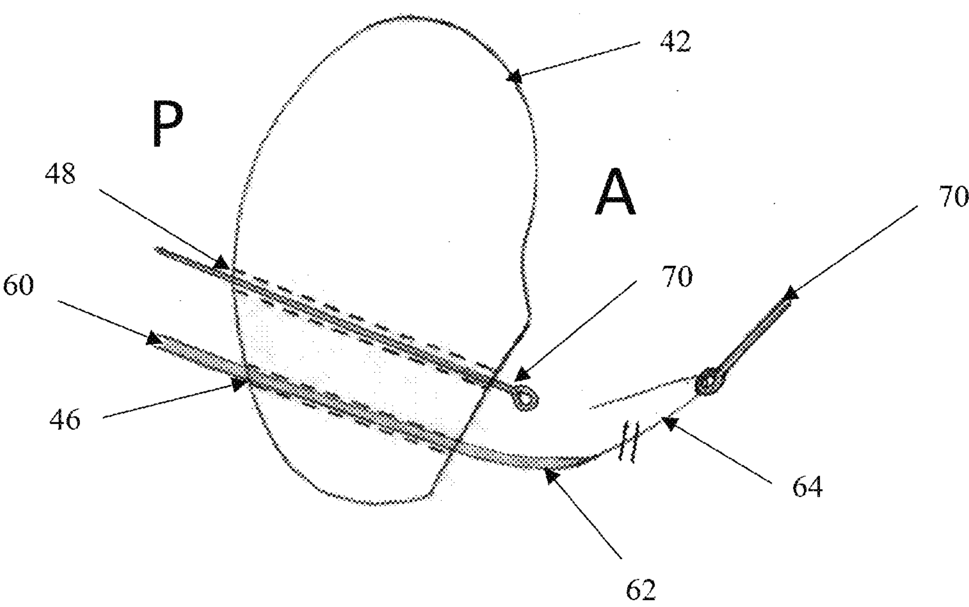
FIG. 6 is a schematic showing the surgical ribbon cable according to an embodiment of the present disclosure passed through the first pilot hole formed in the glenoid.

FIGS. 5 and 6 exemplify the use of the elastomeric ribbon 60 during a surgical procedure, such as an arthroscopic glenoid augmentation surgery. As shown in FIG. 5, a shuttling suture 70, for example, nitinol wire, may be passed through each of the pilot holes 46, 48 from the posterior side P to the anterior side A. In one embodiment, the shuttling suture 70 is passed through the drill guide 10. The shuttling suture 70 should have a sufficient length so that the ends of the shuttling suture 70 may be hemostated together. The elastomeric ribbon 60 may be passed through the shuttling suture 70. As illustrated in FIG. 6, the tail end portion 64 is inserted through the shuttling suture 70 positioned in pilot hole 46. The tail end portion 64 is passed through pilot hole 46 from the posterior side P to the anterior side A, thereby pulling the body portion 62 of the elastomeric ribbon 60 therethrough, as shown in FIG. 6. Once the elastomeric ribbon 60 is passed through pilot hole 46, it may be inserted through a prepared graft.

Figure 7:
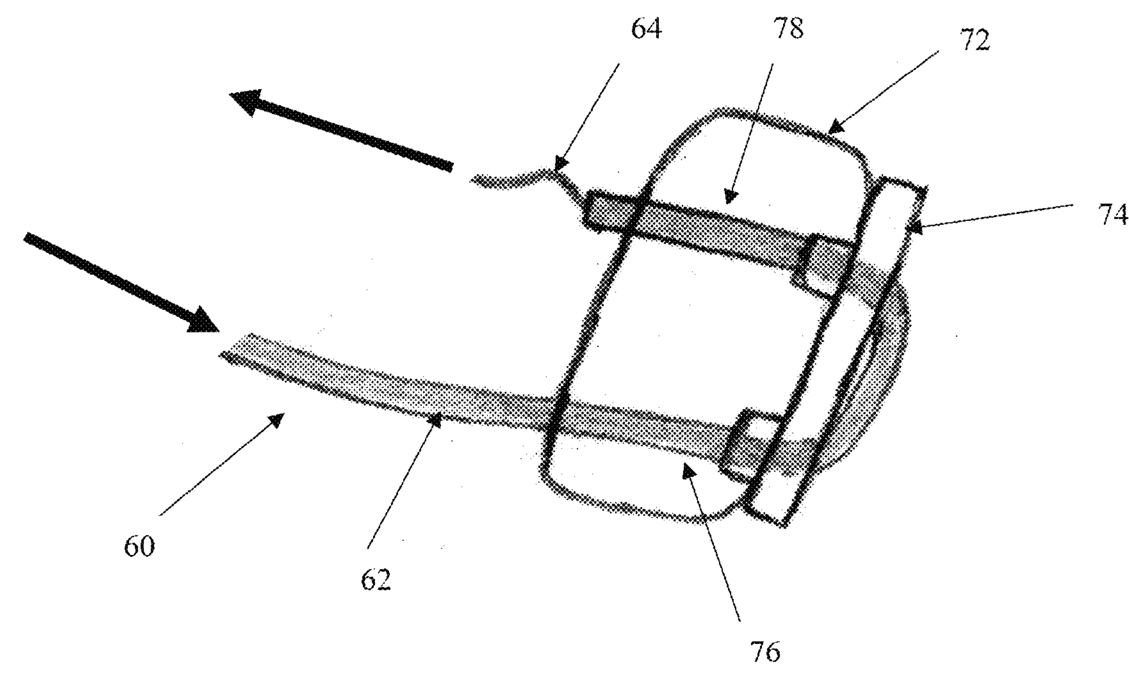
FIG. 7 is a perspective view of a graft attached to a suture glide plate with the surgical ribbon cable passed therethrough according to an embodiment of the present disclosure.
Figure 8:
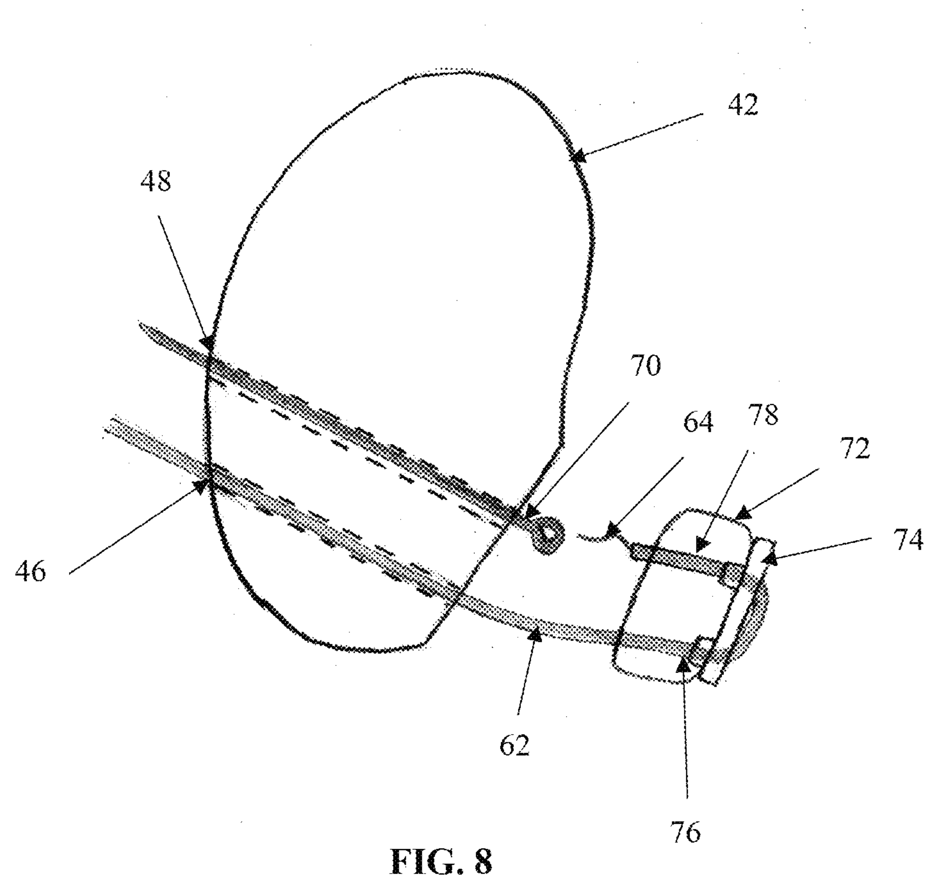
FIG. 8 is a schematic showing the surgical ribbon cable passed through the first pilot hole, the graft, and the suture glide plate before insertion through the second pilot hole.
Figure 9:
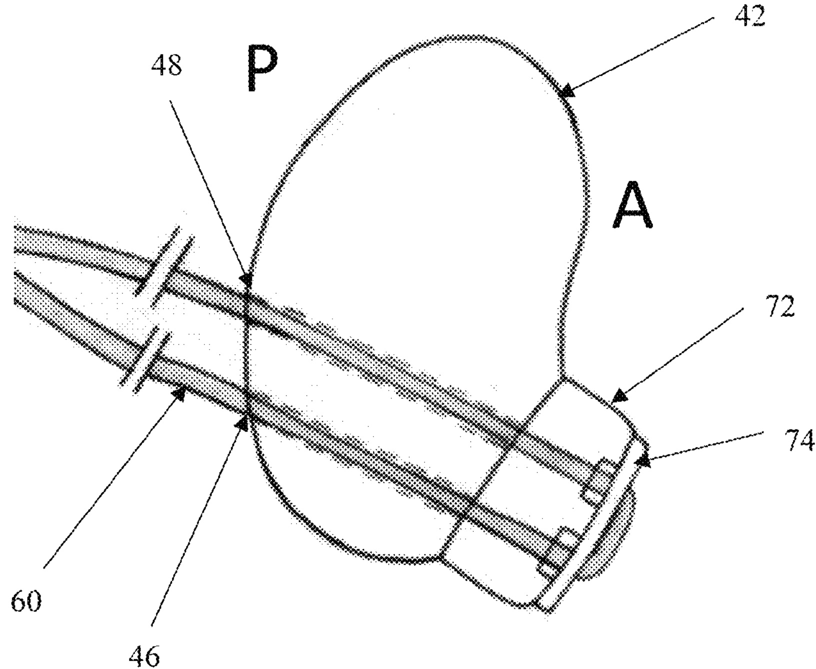
FIG. 9 is a schematic showing the surgical ribbon cable passed through both pilot holes with the graft and suture glide plate attached to the glenoid.

FIGS. 7, 8, and 9 show the elastomeric ribbon 60 inserted through an exemplary graft 72 and suture glide plate 74. As shown in FIG. 7, the graft 72 is operatively attached to the suture glide plate 74 at holes 76, 78 that extend longitudinally therethrough the graft 72 and the suture glide plate 74. The suture glide plate 74 may be anchored to the graft 72, as shown and described in U.S. patent application Ser. No. 17/006,370, filed on Aug. 28, 2020, the entire disclosure of which is incorporated by reference herein. While the suture glide plate 74 has been shown and described herein as having two holes for attachment to the graft 72, the suture glide plate 74 may be configured to have a single hole for use with a single linear construct, as described in more detail below. The elastomeric ribbon 60 is inserted into hole 76 and passed through the graft 72 and suture glide plate 74. The elastomeric ribbon 60 is then looped around and passed back through the suture glide plate 74 and the graft 72 via hole 78. As illustrated in FIG. 8, the tail end portion 64 of the elastomeric ribbon 60 is passed through the shuttling suture 70 for insertion into pilot hole 48. The elastomeric ribbon 60 may then be shuttled through the glenoid 42 from the anterior side A to the posterior side P via pilot hole 48, as shown in FIG. 9.

As illustrated in FIG. 9, the graft 72 is aligned with the glenoid 42 such that the graft 72 physically contacts the glenoid 42. In this embodiment, the graft 72 may be delivered through an anterior portal, such as an anterior cannula, into the shoulder. The graft 72 can be aligned with the glenoid 42 by pulling on the posterior ends of the elastomeric ribbon 60 and pushing the graft 72 into the shoulder. In some embodiments, a soft tissue spreading device (not shown) may be used to maintain an opening in the soft tissue to allow for insertion of the graft 72 without the soft tissue catching the graft 72. Any soft tissue spreading device known in the art may be used in accordance with the present disclosure. For example, soft tissue retractors, meniscal sled devices, or hip scope sled devices may be used to maintain an opening in the soft tissue.

Tensioner & Crimping Device

The present disclosure provides a novel tensioner and crimping device. The tensioner applies tension to a surgical cable, such as the elastomeric ribbon described above, once it has been wrapped around the bone fragments, such that the surgical cable applies a compressive force to the bone fragments to promote healing. The crimping device locks the surgical cable in place with a crimping member, which allows for the tensioner and crimping device to be removed.

Figure 10:
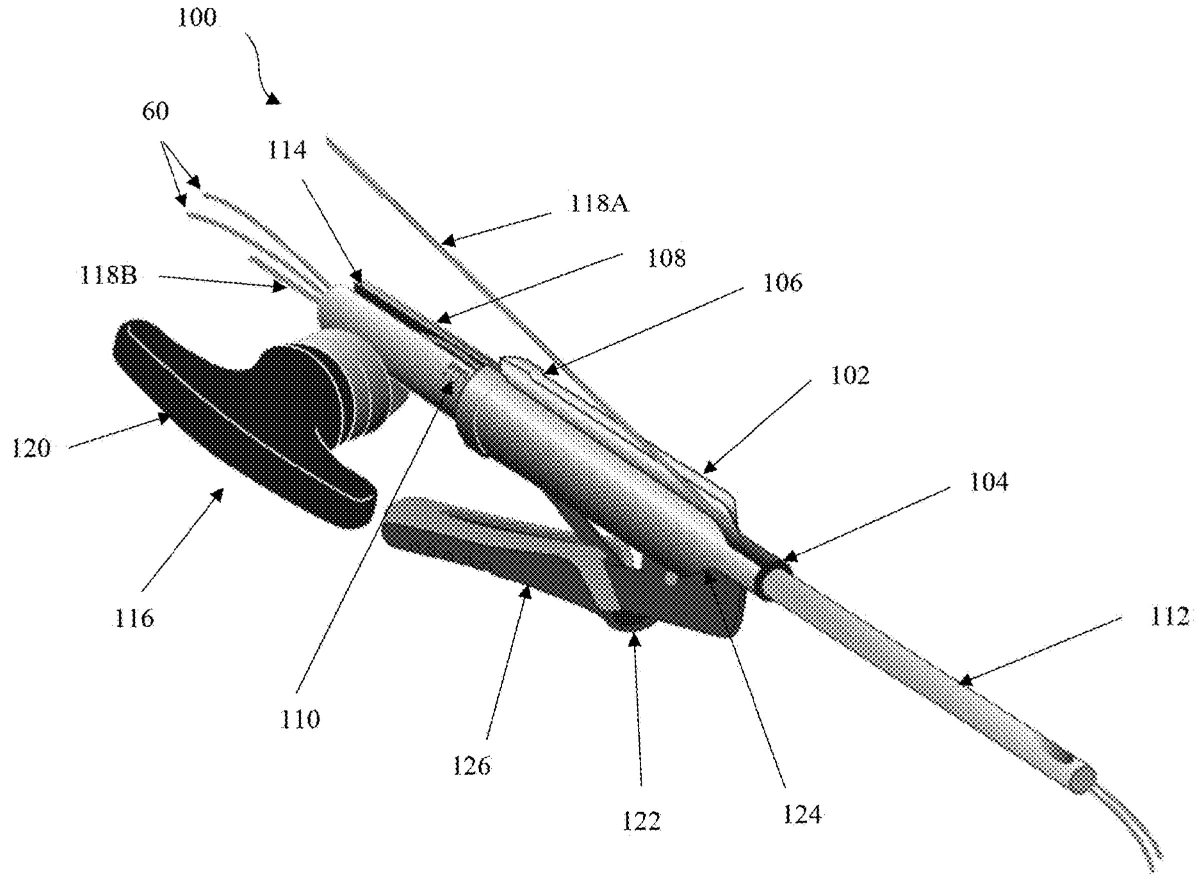
FIG. 10 is a perspective view of a tensioner and crimping device according to an exemplary embodiment of the present disclosure.

FIG. 10 shows a combined tensioner and crimping device 100 according to an exemplary embodiment of the present disclosure. The tensioner and crimping device 100 includes a generally elongated cylindrical housing 102 having a distal end 104 and a proximal end 106. A cylindrical extension 108 is received in the proximal end 106 of the cylindrical housing 102. The cylindrical extension 108 may have a plurality of tension readings 110 for measuring the amount of tension applied to the surgical cable. A nose 112 is fittingly received in the distal end 104 of the cylindrical housing 102. The nose 112 has a length sufficient to fully extend through the cannula during the arthroscopic surgery. For instance, the nose 112 may have a length of about 7 centimeters to about 14 centimeters. In another embodiment, the nose 112 may have a length of about 9 centimeters to about 12 centimeters. For example, the nose 112 may have a length of about 10 centimeters. The end of the nose 112 opposite the cylindrical housing 102 allows for the surgical cable, such as the elastomeric ribbon 60, to be inserted therein. In one embodiment, the end of the nose 112 is generally flat and planar, which provides for better engagement with the glenoid 42 when the nose 112 is inserted through the cannula.

A central bore 114 extends longitudinally through the nose 112, the cylindrical housing 102, and the cylindrical extension 108. The central bore 114 is sized to receive a surgical cable, such as the elastomeric ribbon 60, therethrough. A free end of the elastomeric ribbon 60 is inserted through the nose 112 and into the central bore 114, as shown in FIG. 10. The free end of the elastomeric ribbon 60 is pulled through the central bore 114 for engagement with a tensioning mechanism 116. Wires 118A and 118B also extend through the central bore 114. As will be described in more detail below, wires 118A and 118B hold a crimping member (not shown) in position within the nose 112.

As illustrated in FIG. 10, the combined tensioner and crimping device 100 includes the tensioning mechanism 116 operatively attached to the cylindrical extension 108. The tensioning mechanism 116 includes a manually rotatable tightening knob 120. The tightening knob 120 can be rotated to impose tension upon the surgical cable, such as the elastomeric ribbon 60, when the surgical cable is inserted therethrough, as shown in FIG. 10. Tension applied to the surgical cable allows for the cable to secure the bone graft to the glenoid. The tensioning mechanism 116 has a ratchet feature (not shown) which has the ability to steadily increase the tension in the surgical cable. As the tightening knob 120 is rotated, the ratchet feature raises the tension in the surgical cable and removes any slack so that the cable may be tightened around the bone fragments. The tightening knob

120 also allows for sequential tensioning, using the tension readings 110, so that different amounts of tension can be applied based on the surgical technique being utilized.

The combined tensioner and crimping device 100 also includes a lever actuator 122 for securing a crimping member once the appropriate tension is applied to the surgical cable. In one embodiment, the crimping member (not shown) is carried within the nose 112. The crimping member may be crimped using lever actuator 122 in order to preserve the tension in the cable wrapped around the bone fragments and allow the device 100 to be withdrawn. In the illustrated embodiment, the lever actuator 122 is operatively mounted on a bottom surface 124 of the cylindrical housing 102. The lever actuator 122 is operatively connected to a shaft (not shown) housed within the central bore 114 that moves longitudinally therein. The lever actuator 122 includes a handle 126 that may be mechanically biased. The handle 126 is depressed, the lever actuator 122 moves the shaft longitudinally within the central bore 114 in a forward direction toward the crimping member. As will be described below, the shaft locks the crimping member in place to preserve the tension applied in the surgical cable.

Figure 11:
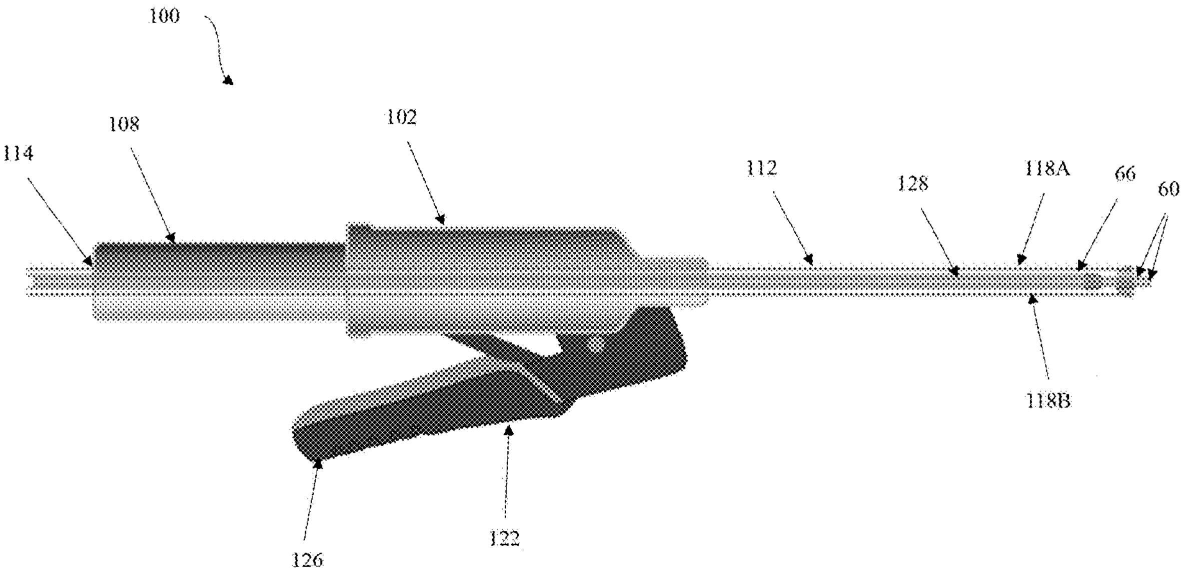
FIG. 11 is a cross-sectional view of the tensioner and crimping device according to an embodiment of the present disclosure.

FIG. 11 is a cross-sectional view of the combined tensioner and crimping device 100. As shown in FIG. 11, the central bore 114 is dimensioned to house a shaft 128 that moves longitudinally therein to secure the crimping member 66. The shaft 128 is operably connected to the lever actuator 122 and moves longitudinally within the central bore 114 when the lever actuator 122 is triggered. The crimping member 66 is carried within the nose 112 at the end of the nose 112 opposite the cylindrical housing 102. The crimping member 66 is held in place by the wires 118A and 118B. Wire 118A and wire 118B extend longitudinally through the nose 112, the cylindrical housing 102, and the cylindrical extension 108 such that free ends of the wires 118A and 118B may be exposed, as shown in FIGS. 10 and 11. The wires 118A and 118B extend along opposing sides of the shaft 128 in a parallel configuration. However, as will be apparent to one of ordinary skill in the art, any configuration and number of wires may be used so long as the crimping member is sufficiently held in position within the nose 112. Wires 118A and 118B may have threaded ends configured for insertion into threaded holes on the crimping member 66, as will be described in more detail below.

Figure 12:
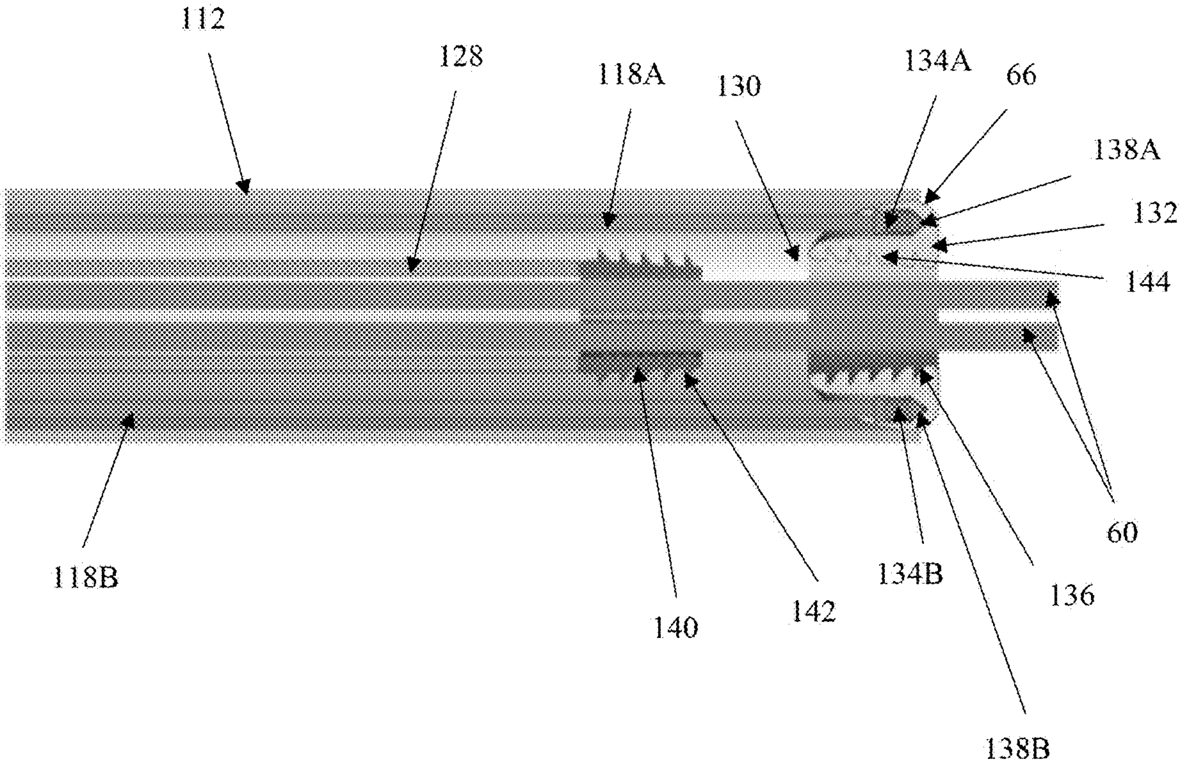
FIG. 12 is a partial cross-sectional view of a nose of the tensioner and crimping device according to an embodiment of the present disclosure.

FIG. 12 is a cross-sectional view of the nose 112 with the shaft 128 and the crimping member 66 positioned within the central bore 114. As illustrated in FIG. 12, the crimping member 66 is dimensioned to sit within the nose 112. The crimping member 66 has a curved front end 130 and a generally flat back end 132. The back end 132 of the crimping member 66 is configured to align with the end of the nose 112 so that, when the nose 112 is inserted through the cannula, the back end 132 is positioned up against the bone fragment. The crimping member 66 also includes internally threaded holes 138A and 138B on opposing sides of the crimping member 66 in parallel alignment with one another. The internally threaded holes 138A and 138B are configured for threaded engagement with each of the threaded ends 134A and 134B of the wires 118A and 118B, respectively. As illustrated in FIG. 12, the threaded ends 134A and 134B of the wires 118A and 118B are screwed into the internally threaded holes 138A and 138B. The crimping member 66 may be formed of any material suitable for surgical procedures. For example, the crimping member 66 may be formed of stainless steel or titanium. The crimping member 66 may be dimensioned to be retained within the nose 112. In one embodiment, the back end 132 of the crimping member 66 may have a width of about 2 mm to about 6 mm. In another embodiment, the back end 132 of the crimping member 66 may have a width of about 3 mm to about 5 mm. For instance, the back end 132 of the crimping member 66 may have a width of about 4 mm.

The crimping member 66 is designed for engagement with the shaft 128 for securing the crimping member 66 against the bone fragment once the appropriate tension is applied to the surgical cable. In this embodiment, the shaft 128 includes a wedge member 140 attached thereto that is configured for engagement with a female receptacle 136 located in the center of the crimping member 66. The wedge member 140 includes a plurality of barbs 142 extending radially therefrom. The plurality of barbs 142 are configured for engagement with a plurality of corresponding grooves 144 on the female receptacle 136. In this embodiment, when the shaft 128 is actuated by the lever actuator 122, the wedge member 140 moves longitudinally in a forward direction to a position in which the wedge member 140 is engaged within the female receptacle 136. Once the wedge member 140 is engaged with the female receptacle 136, the wedge member 140 may be released from the shaft 128 and locked within the crimping member 66. In this embodiment, the wedge member 140 is releasably secured to the shaft 128. For example, the wedge member 140 may be releasably secured to the shaft 128 by a magnetic interface. The magnetic interface may be any type of weak magnet that will not result in any significant resistance to retracting the shaft 128 when it is removed from the crimping member 66 (after the wedge member 140 has been released). In another embodiment, the wedge member 140 may be releasably secured to the shaft 128 by a threaded connection. In still another embodiment, the wedge member 140 may be releasably secured to the shaft 128 using a clasp. In yet another embodiment, the wedge member 140 may be releasably secured to the shaft 128 using an adhesive.

In the illustrated embodiment, the wedge member 140 and the female receptacle 136 include five barbs and five corresponding grooves, respectively, on each side. However, those skilled in the art will appreciate that the wedge member 140 and the female receptacle 136 may include any number of barbs 142 and corresponding grooves 144 deemed suitable for establishing a sufficient connection with one another. As illustrated in FIG. 12, the wedge member 140 and the female receptacle 136 are hollow such that the surgical cable, such as the elastomeric ribbon 60, can be inserted therethrough and pulled through the shaft 128 (which is located within the central bore 114). In one embodiment, the wedge member 140 may include a one-way channel that prevents the elastomeric ribbon 60 from falling through the crimping member 66 once inserted therethrough.

Figure 13A:
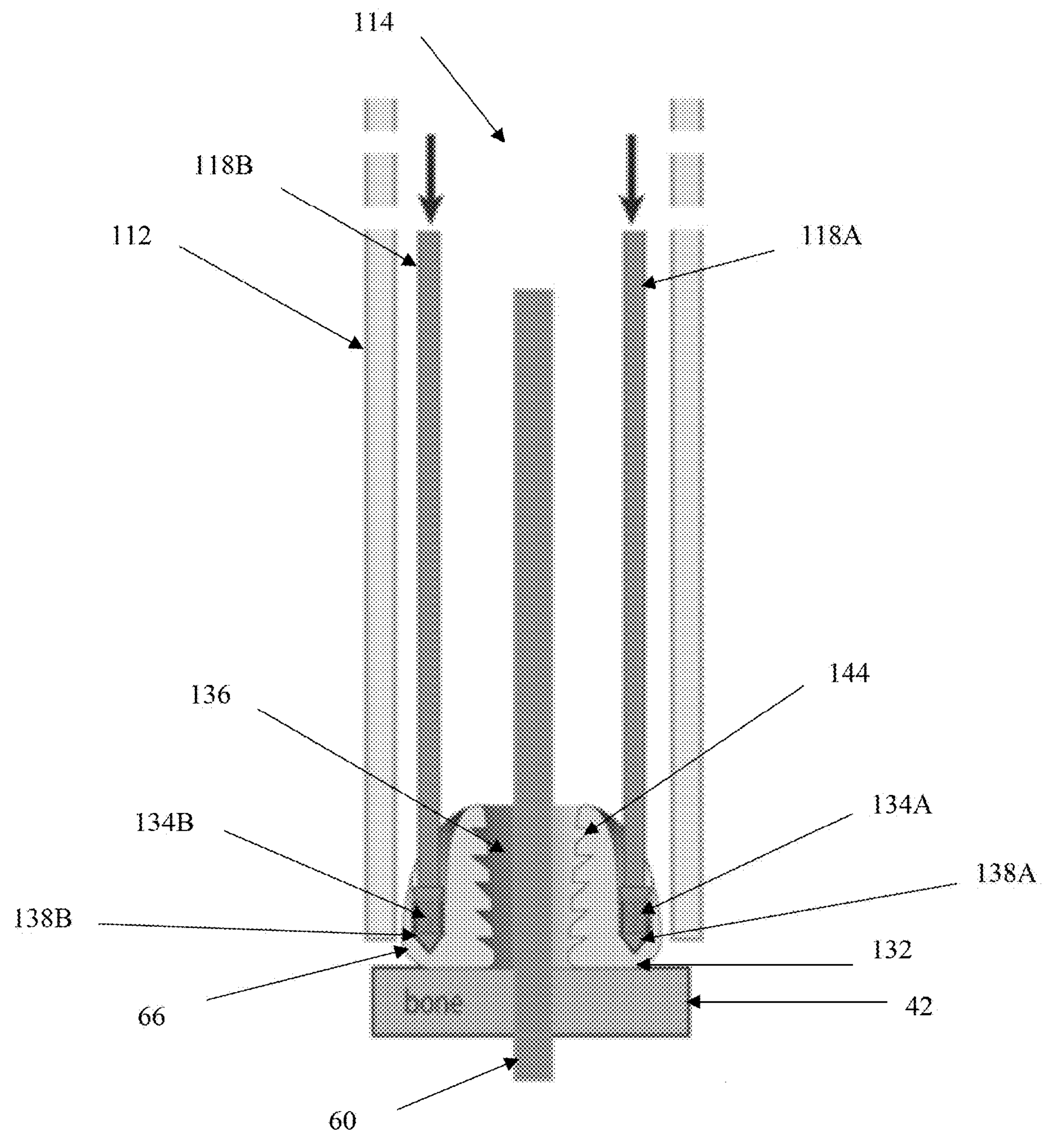
FIGS. 13A-13C are schematics showing the tensioning and crimping mechanisms of the tensioner and crimping device according to an embodiment of the present disclosure.
Figure 13B:
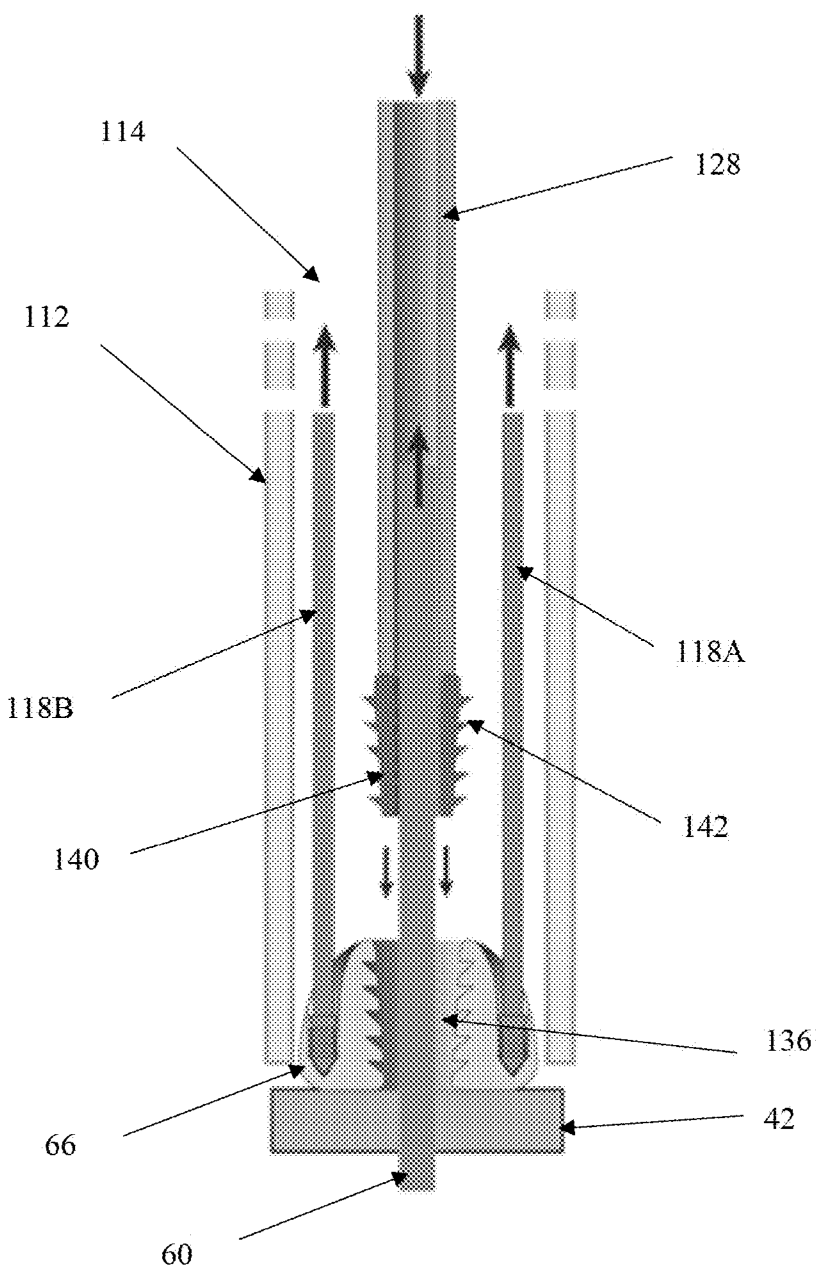
Figure 13C:
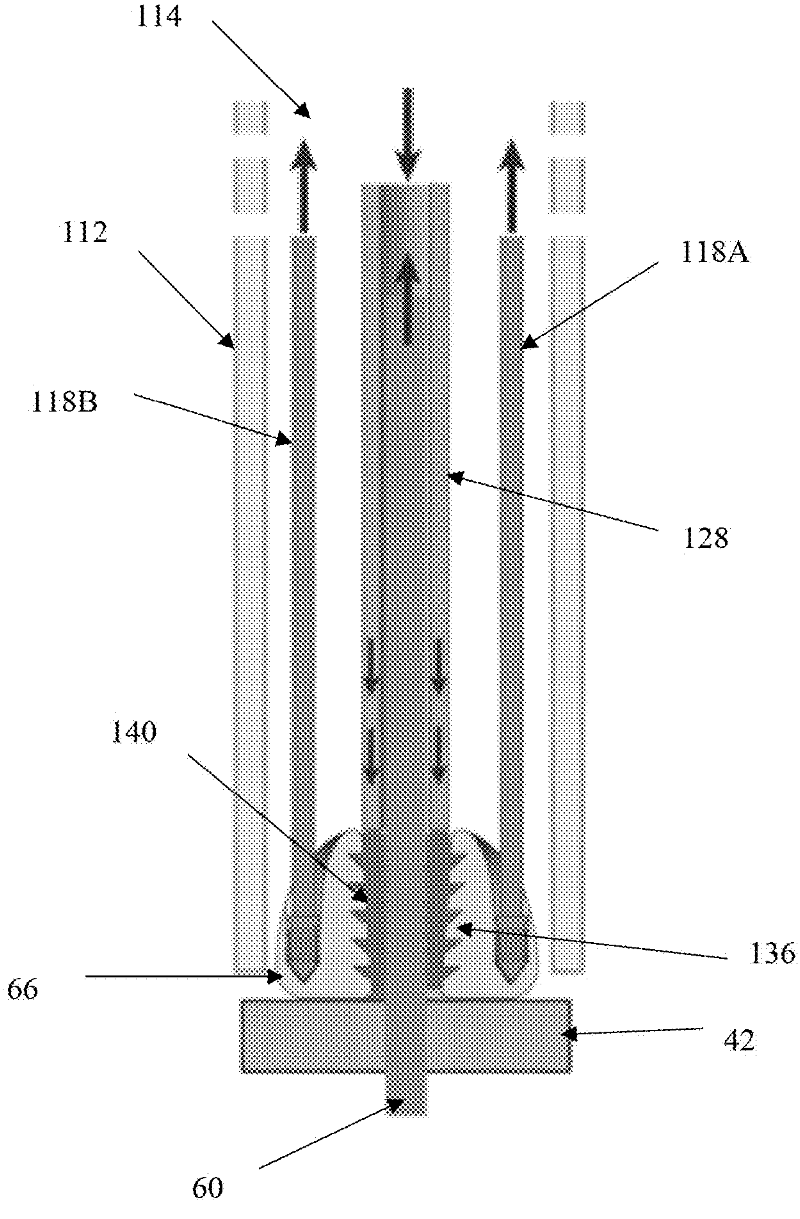

FIGS. 13A-13C show the tensioning and crimping mechanisms of the tensioner and crimping device 100 in use. FIG. 13A is an internal view of the nose 112 positioned within the cannula with the back end 132 of the crimping member 66 in direct engagement with the glenoid 42. As shown in FIG. 13A, the threaded ends 134A and 134B of the wires 118A and 118B are screwed into the internally threaded holes 138A and 138B on the crimping member 66 to hold the crimping member 66 in place before the wedge member 140 is inserted therein. A free end of the elastomeric ribbon 60 is pulled through the crimping member 66 and is ready for tensioning.

The arrows depicted in FIG. 13B represent the tensioning and crimping movement provided by the tensioner and crimping device 100. The free end of the elastomeric ribbon 60 is passed through the central bore 114, and more specifically, through the shaft 128. As shown by the upward arrow, the tensioning mechanism 116 is used to apply tension upon the elastomeric ribbon 60. The tension applied to the elastomeric ribbon 60 allows for the elastomeric ribbon 60 to secure the bone graft to the glenoid 42. Once the elastomeric ribbon 60 is tensioned to the appropriate setting, the surgeon or operator of the device 100 may depress the handle 126 of the lever actuator 122 to move the shaft 128 and wedge member 140 attached thereto in a forward direction (as represented by the downward arrow) to engage the crimping member 66.

FIG. 13C shows the shaft 128 and the wedge member 140 fully engaged with the crimping member 66. As illustrated in FIG. 13C, the plurality of barbs 142 on the wedge member 140 are engaged within the plurality of corresponding grooves 144 on the female receptacle 136. Once the wedge member 140 is engaged within the female receptacle 136 and the desired tension has been achieved, the wedge member 140 may be released from the shaft 128 to retain the elastomeric ribbon 60 in a permanently tensioned configuration. Wires 118A and 118B may be disengaged, for instance, unscrewed, from the crimping device 66 and the tensioner and crimping device 100 may be removed from the cannula.

Figure 13D:
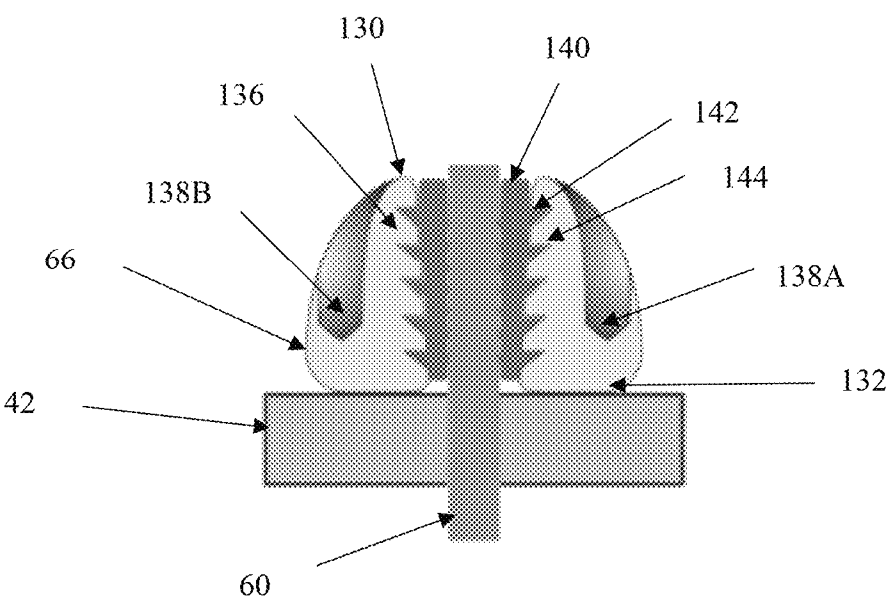
FIG. 13D is a schematic showing the surgical ribbon cable and a crimping member locked in place against the glenoid according to an embodiment of the present disclosure.

FIG. 13D shows the elastomeric ribbon 60 and the crimping member 66 locked in place against the glenoid 42. As shown in FIG. 13D, the wedge member 140 is inserted within the female receptacle 136 of the crimping member 66, which locks the elastomeric ribbon 60 to the crimping member 66. The force applied by the elastomeric ribbon 60 holds the crimping member 66 against the glenoid 42. The elastomeric ribbon 60 may be cut to shorten the length of any excess elastomeric ribbon 60. Conventional cable cutters or suture cutters, such as broad based suture tape cutters, may be used to cut the elastomeric ribbon 60. The cable cutters used in accordance with the present disclosure should have sufficient strength to cut the elastomeric ribbon 60 and be suitable for arthroscopic procedures such as those described herein.

It should be understood that the tensioner and crimping device 100 is exemplary. A tensioner and crimping device of the present disclosure may be realized in other mechanical arrangements that apply a desired tension to an elastomeric member and preserve the applied tension by fixing the elastomeric member in place, for example by mechanically applying a crimp or other lock to the elastomeric member.

Figure 14A:
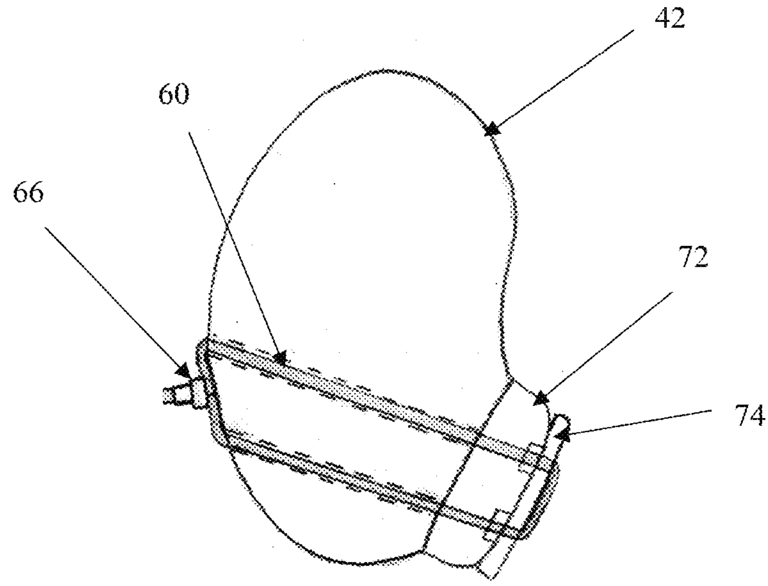
FIG. 14A is a schematic showing a final construct of an arthroscopic glenoid augmentation surgery according to an embodiment of the present disclosure.

FIG. 14A shows a final construct of a repaired glenoid according one embodiment of the present disclosure. As illustrated in FIG. 14A, the elastomeric ribbon 60 is wrapped around the glenoid 42 and the graft 72, such that the elastomeric ribbon 60 applies a compressive force to the bone fragments to promote healing. The elastomeric ribbon 60 is tensioned and secured using the tensioning and crimping device 100 of the present disclosure and is locked in place on the glenoid 42 with the crimping member 66.

Figure 14B:
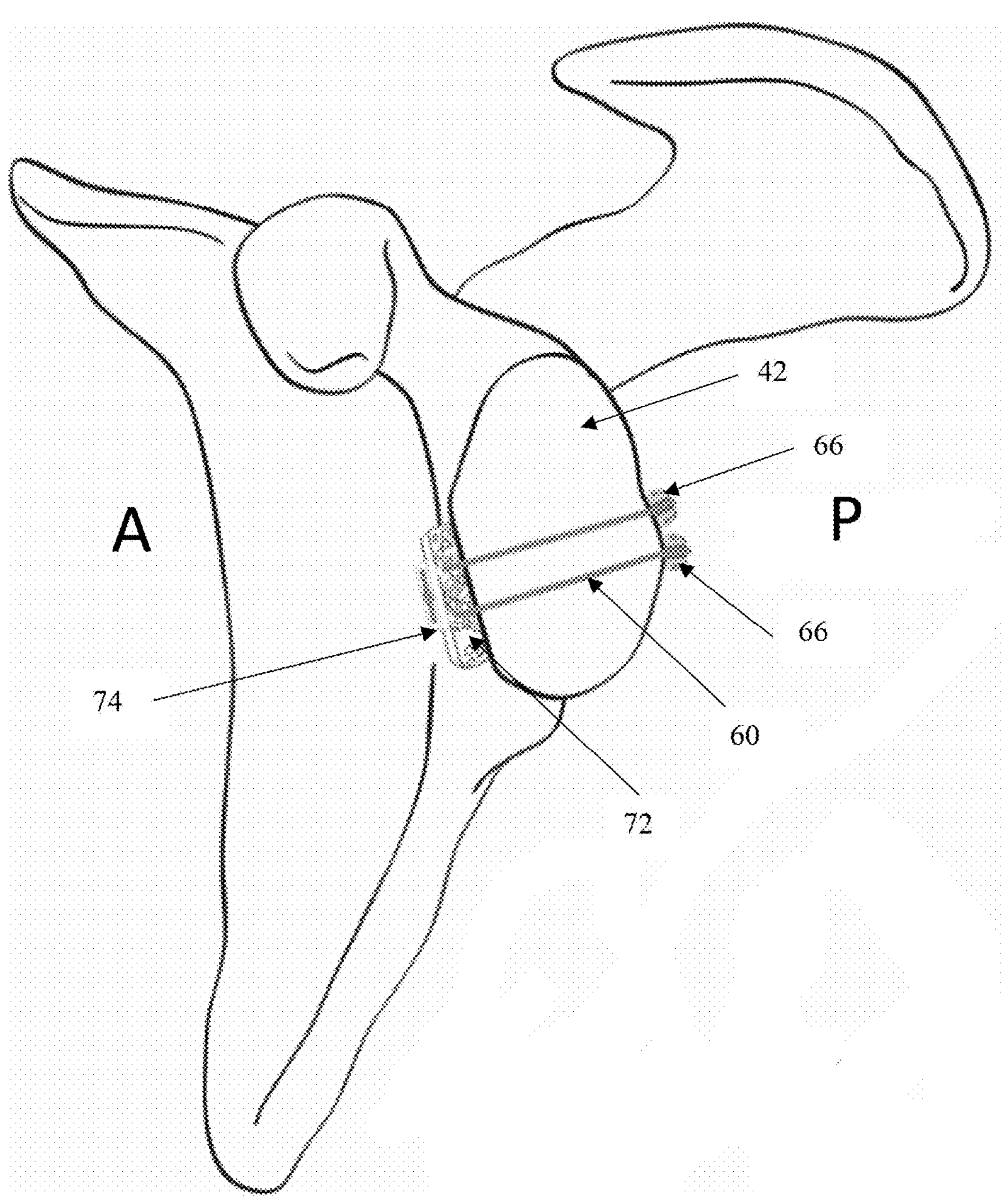
FIG. 14B is a schematic showing a final construct of an arthroscopic glenoid augmentation surgery according to another embodiment of the present disclosure.

FIG. 14B shows a final construct of a repaired glenoid according to another embodiment of the present disclosure. In the illustrated embodiment, two crimping members 66 are used to secure the graft 72 to the glenoid 42. In this embodiment, the elastomeric ribbon 60 is passed through the first pilot hole 46, the suture glide plate 74, and the second pilot hole 48. As shown in FIG. 14B, each end of the elastomeric ribbon 60 is then tensioned and secured using the tensioning and crimping device 100 of the present disclosure and is locked in place on the glenoid 42 with the two crimping members 66.

Figure 14C:
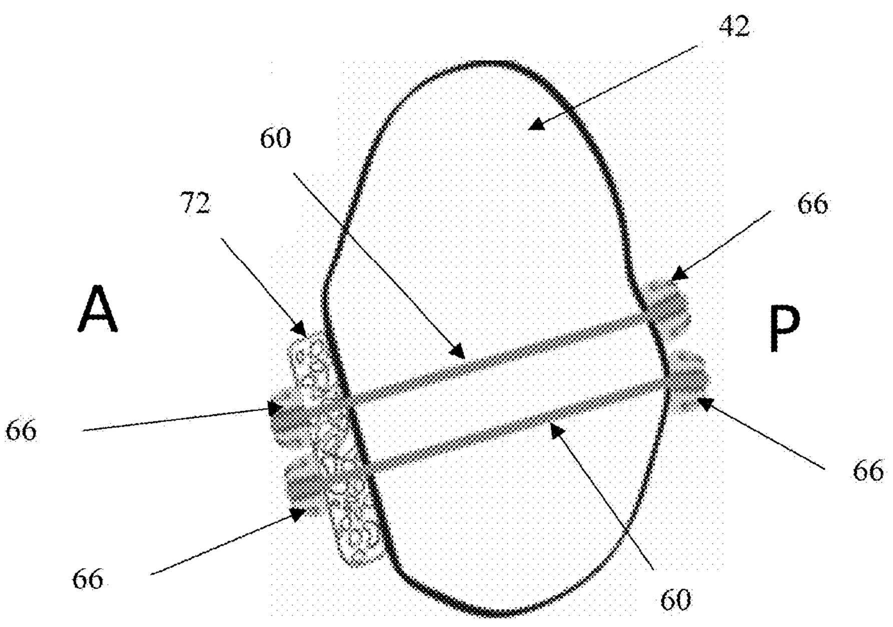
FIG. 14C is a schematic showing a final construct of an arthroscopic glenoid augmentation surgery according to still another embodiment of the present disclosure.
Figure 14D:
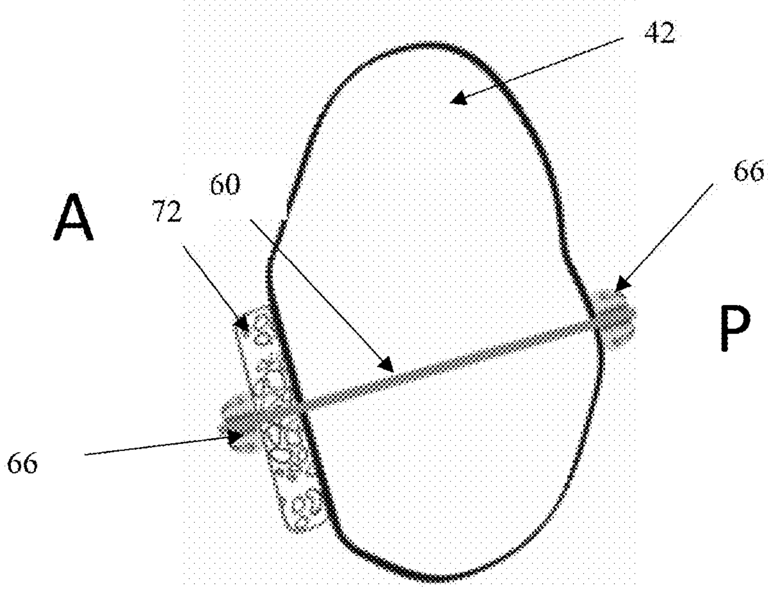
FIG. 14D is a schematic showing a final construct of an arthroscopic glenoid augmentation surgery according to yet another embodiment of the present disclosure.

FIGS. 14C and 14D show final constructs of a repaired glenoid according to yet another embodiment of the present disclosure. As shown in the illustrated embodiments, a linear construct may be utilized to secure the graft 72 to the glenoid 42. The linear constructs are advantageous in that they can dispense of the need to use the suture glide plate 74. In other embodiments, the linear constructs may utilize suture glide plates having a single hole (as described above). As shown in FIG. 14C, two separate elastomeric ribbons 60 are passed through each of the pilot holes 46, 48 and are secured by crimping members 66 positioned on both the anterior A and posterior P sides. In other embodiments, as shown in FIG. 14D, a single pilot hole, for example, the first pilot hole 46, may be utilized where the elastomeric ribbon 60 is passed through the pilot hole 46 and is secured by crimping members 66 positioned on both the anterior A and posterior P sides. The elastomeric ribbons 60 are tensioned and secured using the tensioning and crimping device 100 of the present disclosure and are locked in place on the glenoid 42 with the crimping members 66.

Figure 14E:
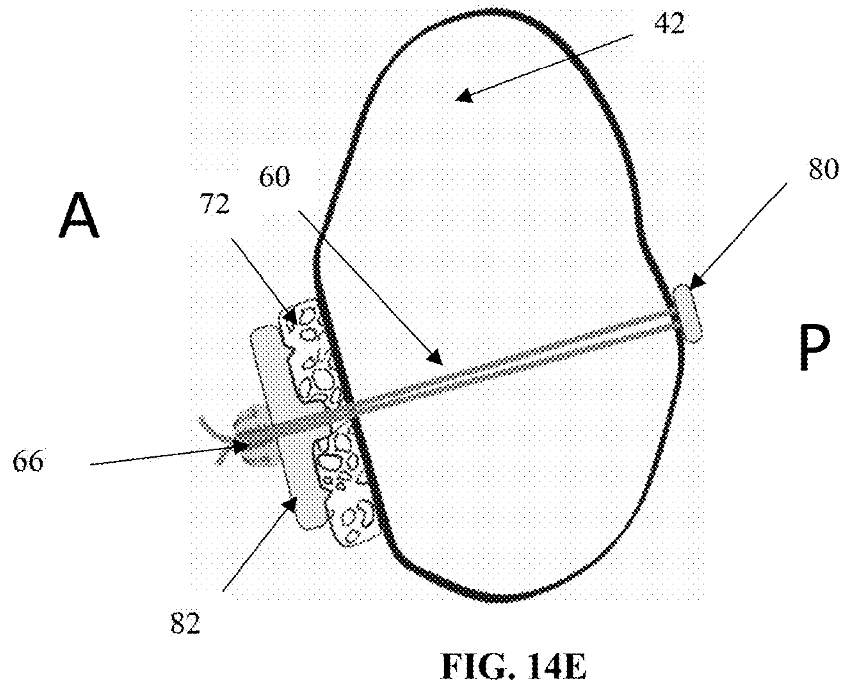
FIG. 14E is a schematic showing a final construct of an arthroscopic glenoid augmentation surgery according to yet another embodiment of the present disclosure.

In yet another embodiment, as shown in FIG. 14E, a single pilot hole, for example, the first pilot hole 46, may be utilized where a narrow oblong and flippable fixation device 80, such as an Endobutton, is secured to the elastomeric ribbon 60 and is passed through the pilot hole 46. Once the fixation device is passed through the pilot hole to a distal side of the bone (such as posterior side P), the device may be flipped, and the elastomeric ribbon 60 is then tensioned and secured by a single crimping member 66 positioned on the proximate side of the bone (such as anterior side A) from which the pilot hole 46 was drilled. The elastomeric ribbon 60 may be tensioned and secured using the tensioning and crimping device 100 of the present disclosure and may be locked in place with the crimping member 66. This embodiment is suitable to procedures that secure grafts as well as more general procedures requiring fixation of bone and/or tendon that do not involve grafts. In addition, in a preferred embodiment (as shown in FIG. 14E), an optional orthopedic plate 82 may be used in conjunction with the crimping member 66 to distribute the compressive force across a graft, a surface of a bone, or other member to reduce the risk of a fracture or other impairment caused by the compression itself. It should be understood that in other embodiments, a suture of any kind may be used with the Endobutton-type fixation device. The suture may be tensioned and crimped with the tensioning and crimping device 100 of the present disclosure and locked in place with the crimping member 66, or with another suitable tensioning device and crimp sufficient to secure the suture and maintain tension to hold the Endobutton fixation device in place.

Methods of Use

Figure 15:
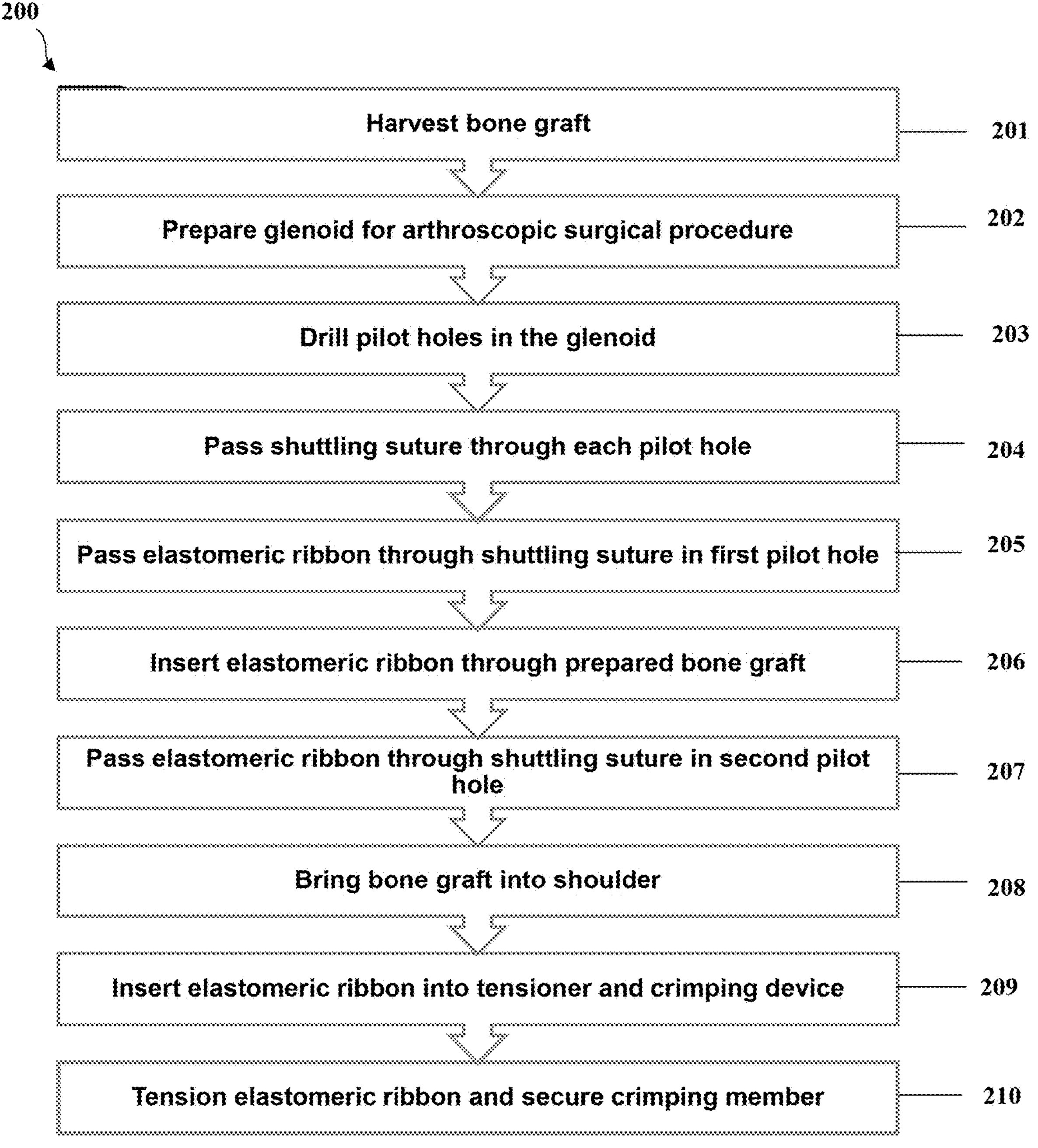
FIG. 15 is a flowchart illustrating the steps according to a method for arthroscopic glenoid augmentation surgery in accordance with an embodiment of the present disclosure.

The present disclosure provides methods for arthroscopic procedures. In one embodiment, the present disclosure provides methods for arthroscopic glenoid augmentation surgery. Although the techniques described herein are specific for arthroscopic procedures, one of ordinary skill in the art would readily understand that the techniques may be used for open procedures as well. FIG. 15 is a flowchart illustrating the steps according to a method 200 for arthroscopic glenoid augmentation surgery according to an exemplary embodiment of the present disclosure.

At step 201, the method begins by harvesting a bone graft for reconstructing the glenoid. In one embodiment, the bone graft is harvested. For instance, the bone graft may be an autograft and may be harvested from the distal clavicle, iliac crest, distal tibia, or coracoid. In another embodiment, the bone graft may be an allograft. Once the bone graft is harvested, the graft can be prepared separately for insertion into the patient. At step 202, the glenoid is prepared for the arthroscopic surgical procedure. A posterior portal is opened for a generally forward-directed cannula (not shown). The forward-directed cannula provides access to the surgical site. In this embodiment, the labrum above and below the bony augmentation region can be prepared for surgery. For example, the labrum may be freed from the glenoid neck to restore tension in the capsule once the labrum is placed in its proper position. During preparation, soft tissue may also be removed so that the labrum is able to heal to the glenoid.

After the glenoid has been prepared, substantially parallel pilot holes can be drilled into the glenoid using, for example, the drill guide of the present disclosure (step 203). In this embodiment, the drill guide described herein can be inserted through the posterior cannula into the proximity of the surgical site. As discussed above, aligning the tab of the drill guide along the rim of the glenoid provides for precise placement of the drill guide and the corresponding pilot holes. Guide wire may be inserted through the wire guide opening and engaged with the glenoid to provide additional stability of the drill guide. Two pilot holes can be drilled into the glenoid from the posterior side to the anterior side using the procedure discussed above with respect to the drill guide.

At step 204, a shuttling suture, such as nitinol wires, can be passed through each of the pilot holes from the posterior side to the anterior side. The shuttling suture should have a sufficient length so that the ends of the shuttling suture may be hemostated together. At step 205, a free end of the elastomeric ribbon is passed through the shuttling suture. In one embodiment, the tail end portion is inserted through the shuttling suture positioned in the first pilot hole from the posterior side to the anterior side, thereby pulling the body portion of the elastomeric ribbon therethrough.

Once the elastomeric ribbon is passed through the first pilot hole, it may exit the surgical site through an anterior portal and be inserted through the prepared bone graft (step 206) outside of the shoulder. In some embodiments, the free end of the elastomeric ribbon is passed through a hole on the posterior side of the graft and accompanying anterior suture glide plate, looped around, and passed through the opposite hole of the graft and accompanying suture glide plate back to the other side. The elastomeric ribbon may then be passed back through the anterior portal into the shoulder and shuttled through the glenoid from the anterior side to the posterior side via the second pilot hole (step 207). In other embodiments, the free end of the elastomeric ribbon may be passed through the graft and secured on the anterior side with a crimping member, as shown in FIGS. 14C and 14D, which may dispense of the use of the suture glide plate.

At step 208, once the free end of the elastomeric ribbon is passed through the second pilot hole, the bone graft can be aligned with the glenoid by pulling on the posterior ends of the elastomeric ribbon and pushing the graft into the shoulder through the anterior portal to position the bone graft into the desired location on the glenoid. In some embodiments, a soft tissue spreading device may be used to maintain an opening in the soft tissue to allow for insertion of the graft without the soft tissue catching the graft.

Once the bone graft is aligned with the glenoid, the elastomeric cable can be tensioned and secured using, for example, the tensioner and crimping device of the present disclosure. At step 209, the tensioner and crimping device of the present disclosure is inserted into the posterior cannula so that the free ends of the elastomeric ribbon can be inserted into the device. At step 210, the tensioning mechanism of the tensioner and crimping device of the present disclosure is used to apply tension upon the elastomeric ribbon. The tension applied to the elastomeric ribbon allows for the elastomeric ribbon to secure the bone graft to the glenoid. Once the elastomeric ribbon is tensioned to the appropriate setting, the surgeon or operator of the tensioner and crimping device may use the lever actuator to secure the crimping member, which retains the elastomeric ribbon in a permanently tensioned configuration. Indeed, as shown in FIG. 14B, more than one crimping member may be used to retain the elastomeric ribbon in a permanently tensioned configuration. The tensioner and crimping device may then be removed from the cannula. In some embodiments, the elastomeric ribbon may be cut to shorten the length of any excess material. Conventional cable cutters or suture cutters may be used to cut the elastomeric ribbon.

The foregoing description illustrates and describes the processes, manufactures, and other teachings of the present disclosure. Additionally, the disclosure shows and describes only certain embodiments of the processes, manufactures, and other teachings disclosed, but, as mentioned above, it is to be understood that the teachings of the present disclosure are capable of use in various other combinations, modifications, and environments and are capable of changes or modifications within the scope of the teachings as expressed herein, commensurate with the skill and/or knowledge of a person having ordinary skill in the relevant art. The embodiments described hereinabove are further intended to explain certain best modes known of practicing the processes, manufactures, and other teachings of the present disclosure and to enable others skilled in the art to utilize the teachings of the present disclosure in such, or other, embodiments and with the various modifications required by the particular applications or uses. Accordingly, the processes, manufactures, and other teachings of the present disclosure are not intended to limit the exact embodiments and examples disclosed herein. Any section headings herein are provided only for consistency with the suggestions of 37 C.F.R. § 1.77 or otherwise to provide organizational queues. These headings shall not limit or characterize the invention(s) set forth herein.

What is claimed is:

1. A method of performing an arthroscopic bone augmentation surgery, comprising:

drilling a pilot hole into a bone in need of augmentation surgery, wherein the drilling is performed from a first side to a second side;

passing a first end of a surgical cable through the pilot hole from the first side to the second side and into a graft;

securing a first crimping member to the first end of the surgical cable on the first side, wherein the first crimping member is secured to an outer surface of the bone;

passing a second end of the surgical cable through a tensioning and crimping device and into engagement with a tensioning mechanism;

tensioning the surgical cable using the tensioning mechanism to a setting sufficient to apply a compressive force to the bone and the graft;

while maintaining the compressive force, actuating movement of a securing member carried within the tensioning and crimping device toward a second crimping member positioned at a distal end of the tensioning and crimping device;

engaging the securing member with the second crimping member, wherein the securing member comprises a plurality of barbs configured to engage with a plurality of corresponding grooves on the second crimping member; and releasing the securing member from the tensioning and crimping device upon engagement with the second crimping member on the second side to preserve the applied compressive force, wherein the second crimping member and engaged securing member are secured to an outer surface of the graft.

2. The method of claim 1, wherein the first side is a posterior side and the second side is an anterior side.

3. The method of claim 1, wherein the step of tensioning further comprises tensioning the surgical cable to about 400 N to 800 N to provide a continuous active compressive force across the bone and the graft.

4. The method of claim 1, wherein the bone in need of augmentation surgery is a glenoid.

5. The method of claim 1, further comprising creating a posterior portal for insertion of a posterior cannula and an anterior portal for insertion of an anterior cannula.

6. The method of claim 1, wherein the first end of the surgical cable is passed through the pilot hole without forming a loop.

7. The method of claim 1, wherein the drilling step comprises drilling a single pilot hole into the bone in need of augmentation surgery.

8. The method of claim 1, wherein the first crimping member sits flush against the outer surface of the bone and the second crimping member sits flush against the outer surface of the graft.

9. The method of claim 1, wherein the second crimping member and engaged securing member sit flush against the outer surface of the graft.

* * * * *